US012357455B2

(12) United States Patent
Conklin et al.

(10) Patent No.: US 12,357,455 B2
(45) Date of Patent: *Jul. 15, 2025

(54) HYBRID HEART VALVES

(71) Applicant: EDWARDS LIFESCIENCES CORPORATION, Irvine, CA (US)

(72) Inventors: Brian S. Conklin, Orange, CA (US); Qinggang Zeng, Mission Viejo, CA (US); Myron Howanec, Jr., Corona, CA (US); Grace Myong Kim, Seal Beach, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 18/308,439

(22) Filed: Apr. 27, 2023

(65) Prior Publication Data

US 2023/0285145 A1   Sep. 14, 2023

Related U.S. Application Data

(63) Continuation of application No. 16/666,331, filed on Oct. 28, 2019, now Pat. No. 11,654,020, which is a
(Continued)

(51) Int. Cl.
*A61F 2/24*   (2006.01)
(52) U.S. Cl.
CPC .......... *A61F 2/2418* (2013.01); *A61F 2/2409* (2013.01); *A61F 2210/0057* (2013.01);
(Continued)
(58) Field of Classification Search
CPC .................. A61F 2/2409; A61F 2/2418; A61F 2210/0057; A61F 2220/0075;
(Continued)

(56) References Cited

U.S. PATENT DOCUMENTS 3,143,742 A   8/1964 Cromie
3,320,972 A   5/1967 High et al.
(Continued)

FOREIGN PATENT DOCUMENTS

CN   102883684 A   1/2013
EP   0125393 A1   11/1984
(Continued)

OTHER PUBLICATIONS

Krakow, "3F Therapeutics, Inc. Announces the First Clinical Implantation of the 3F Enable Aortic Heart Valve.TM., a Patented, Sutureless Implantation, Replacement Heart Valve Intended to Save Valuable Surgery Time and Reduce Time RelatedComplications . . . " Healthcare Sales & Marketing Network News Feed, Jan. 18, 2005, pp. 1-2.
(Continued)

*Primary Examiner* — Paul B Prebilic
(74) *Attorney, Agent, or Firm* — Guy Cumberbatch

(57) ABSTRACT

A prosthetic heart valve configured to replace a native heart valve and having a support frame configured to be reshaped into an expanded form in order to receive and/or support an expandable prosthetic heart valve therein is disclosed, together with methods of using same. The prosthetic heart valve may be configured to have a generally rigid and/or expansion-resistant configuration when initially implanted to replace a native valve (or other prosthetic heart valve), but to assume a generally expanded form when subjected to an outward force such as that provided by a dilation balloon or other mechanical expander. An inflow stent frame is expandable for anchoring the valve in place, and may have an outflow end that is collapsible to a limited degree for delivery and expandable post-implant to facilitate a valve-in-valve (ViV) procedure. The hybrid heart valves eliminate
(Continued)

earlier structural bands, which both reduces manufacturing time and facilitates a ViV procedure.

20 Claims, 18 Drawing Sheets

Related U.S. Application Data continuation of application No. 15/199,748, filed on Jun. 30, 2016, now Pat. No. 10,456,246.

(60) Provisional application No. 62/188,465, filed on Jul. 2, 2015.

(52) U.S. Cl.
CPC .............. *A61F 2220/0075* (2013.01); *A61F 2230/0069* (2013.01); *A61F 2250/001* (2013.01); *A61F 2250/0018* (2013.01); *A61F 2250/0048* (2013.01); *A61F 2250/006* (2013.01); *A61F 2250/0097* (2013.01)

(58) Field of Classification Search
CPC ........ A61F 2230/0069; A61F 2250/001; A61F 2250/0018; A61F 2250/0048; A61F 2250/006

See application file for complete search history.

(56) References Cited

U.S. PATENT DOCUMENTS

| | | |
|---|---|---|
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,656,185 A | 4/1972 | Carpentier |
| 3,657,744 A | 4/1972 | Ersek |
| 3,686,740 A | 8/1972 | Shiley |
| 3,755,823 A | 9/1973 | Hancock |
| 3,839,741 A | 10/1974 | Haller |
| 4,035,849 A | 7/1977 | Angell et al. |
| 4,055,861 A | 11/1977 | Carpentier et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,164,046 A | 8/1979 | Cooley |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,602,911 A | 7/1986 | Ahmadi et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,147,391 A | 9/1992 | Lane |
| 5,163,955 A | 11/1992 | Love et al. |
| 5,201,880 A | 4/1993 | Wright et al. |
| 5,258,021 A | 11/1993 | Duran |
| 5,258,023 A | 11/1993 | Reger |
| 5,306,296 A | 4/1994 | Wright et al. |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,522 A | 5/1995 | Trott |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,450,860 A | 9/1995 | O'Connor |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,496,336 A | 3/1996 | Cosgrove et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,593,435 A | 1/1997 | Carpentier et al. |
| 5,607,471 A | 3/1997 | Seguin et al. |
| 5,626,607 A | 5/1997 | Malecki et al. |
| 5,628,789 A | 5/1997 | Vanney et al. |
| 5,674,279 A | 10/1997 | Wright et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,776,189 A | 7/1998 | Khalid |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,066 A | 10/1998 | Gross |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |

(56) References Cited

U.S. PATENT DOCUMENTS

| | | |
|---|---|---|
| 5,888,240 A | 3/1999 | Carpentier et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,928,281 A | 7/1999 | Huynh et al. |
| 5,957,949 A | 9/1999 | Leonhardt et al. |
| 5,972,004 A | 10/1999 | Williamson, IV et al. |
| 5,972,030 A | 10/1999 | Garrison et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,059,827 A | 5/2000 | Fenton, Jr. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,264,611 B1 | 7/2001 | Ishikawa et al. |
| 6,322,526 B1 | 11/2001 | Rosenman et al. |
| 6,332,893 B1 | 12/2001 | Mortier et al. |
| 6,348,068 B1 | 2/2002 | Campbell et al. |
| 6,350,282 B1 | 2/2002 | Eberhardt |
| 6,391,054 B2 | 5/2002 | Carpentier et al. |
| 6,406,493 B1 | 6/2002 | Tu et al. |
| 6,419,696 B1 | 7/2002 | Ortiz et al. |
| 6,425,916 B1 | 7/2002 | Garrison et al. |
| 6,454,799 B1 | 9/2002 | Schreck |
| 6,461,382 B1 | 10/2002 | Cao |
| 6,491,624 B1 | 12/2002 | Lotfi |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,726,717 B2 | 4/2004 | Alfieri et al. |
| 6,764,510 B2 | 7/2004 | Vidlund et al. |
| 6,773,457 B2 | 8/2004 | Ivancev et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,858,039 B2 | 2/2005 | McCarthy |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,955,689 B2 | 10/2005 | Ryan et al. |
| 6,966,924 B2 | 11/2005 | Holmberg |
| 6,986,775 B2 | 1/2006 | Morales et al. |
| 7,018,404 B2 | 3/2006 | Holmberg et al. |
| 7,037,333 B2 | 5/2006 | Myers et al. |
| 7,101,395 B2 | 9/2006 | Tremulis et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,261,732 B2 | 8/2007 | Justino |
| 7,276,084 B2 | 10/2007 | Yang et al. |
| 7,294,148 B2 | 11/2007 | McCarthy |
| 7,381,218 B2 | 6/2008 | Schreck |
| 7,393,360 B2 | 7/2008 | Spenser et al. |
| 7,399,315 B2 | 7/2008 | Iobbi |
| 7,452,376 B2 | 11/2008 | Lim et al. |
| 7,462,191 B2 | 12/2008 | Spenser et al. |
| 7,470,285 B2 | 12/2008 | Nugent et al. |
| 7,510,575 B2 | 3/2009 | Spenser et al. |
| 7,524,330 B2 | 4/2009 | Berreklouw |
| 7,534,261 B2 | 5/2009 | Friedman |
| 7,556,646 B2 | 7/2009 | Yang et al. |
| 7,585,321 B2 | 9/2009 | Cribier |
| 7,625,403 B2 | 12/2009 | Krivoruchko |
| 7,780,723 B2 | 8/2010 | Taylor |
| 7,806,927 B2 | 10/2010 | Styrc |
| 7,871,436 B2 | 1/2011 | Ryan et al. |
| 7,998,151 B2 | 8/2011 | St. Goar et al. |
| 8,226,707 B2 | 7/2012 | White |
| 8,246,677 B2 | 8/2012 | Ryan |
| 8,308,798 B2 | 11/2012 | Pintor et al. |
| 8,323,337 B2 | 12/2012 | Gurskis et al. |
| 8,348,998 B2 | 1/2013 | Pintor et al. |
| 8,496,700 B2 | 7/2013 | Edoga et al. |
| 8,500,802 B2 | 8/2013 | Lane et al. |
| 8,696,742 B2 | 4/2014 | Pintor et al. |
| 9,248,016 B2 | 2/2016 | Oba et al. |
| 9,301,836 B2 | 4/2016 | Buchbinder et al. |
| 9,333,100 B2 | 5/2016 | Eberhardt et al. |
| 9,504,563 B2 | 11/2016 | Pintor et al. |
| 9,788,941 B2 | 10/2017 | Hacohen |
| 9,901,448 B2 | 2/2018 | Pintor et al. |
| 9,918,836 B2 | 3/2018 | Hodshon et al. |
| 10,080,653 B2 | 9/2018 | Conklin et al. |
| 10,751,174 B2 | 8/2020 | Conklin et al. |
| 11,065,112 B2 | 7/2021 | Gassler |
| 11,083,574 B2 | 8/2021 | Sievers et al. |
| 2001/0021872 A1 | 9/2001 | Bailey et al. |
| 2001/0021874 A1 | 9/2001 | Carpentier et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0062150 A1 | 5/2002 | Campbell et al. |
| 2002/0123802 A1 | 9/2002 | Snyders |
| 2002/0133226 A1 | 9/2002 | Marquez et al. |
| 2002/0138138 A1 | 9/2002 | Yang |
| 2002/0143386 A1 | 10/2002 | Davila et al. |
| 2002/0151970 A1 | 10/2002 | Garrison et al. |
| 2002/0173842 A1 | 11/2002 | Buchanan |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0033009 A1 | 2/2003 | Gabbay |
| 2003/0036795 A1 | 2/2003 | Andersen et al. |
| 2003/0040792 A1 | 2/2003 | Gabbay |
| 2003/0040793 A1 | 2/2003 | Marquez |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0199971 A1 | 10/2003 | Tower et al. |
| 2003/0236568 A1 | 12/2003 | Hojeibane et al. |
| 2004/0007895 A1 | 1/2004 | Egner-Walter |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |

(56) References Cited

U.S. PATENT DOCUMENTS

| | | |
|---|---|---|
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0249452 A1 | 12/2004 | Adams et al. |
| 2004/0249453 A1 | 12/2004 | Cartledge et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0096739 A1 | 5/2005 | Cao |
| 2005/0131533 A1 | 6/2005 | Alfieri et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137702 A1 | 6/2005 | Haug et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240200 A1 | 10/2005 | Bergheim |
| 2005/0240259 A1 | 10/2005 | Sisken et al. |
| 2005/0251251 A1 | 11/2005 | Cribier |
| 2005/0251252 A1 | 11/2005 | Stobie |
| 2005/0256567 A1 | 11/2005 | Lim et al. |
| 2005/0256568 A1 | 11/2005 | Lim et al. |
| 2005/0261765 A1 | 11/2005 | Liddicoat |
| 2005/0267572 A1 | 12/2005 | Schoon et al. |
| 2005/0278022 A1 | 12/2005 | Lim |
| 2005/0283231 A1 | 12/2005 | Haug et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025857 A1 | 2/2006 | Bergheim et al. |
| 2006/0025858 A1 | 2/2006 | Alameddine |
| 2006/0030885 A1 | 2/2006 | Hyde |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0122692 A1 | 6/2006 | Gilad et al. |
| 2006/0136054 A1 | 6/2006 | Berg et al. |
| 2006/0149360 A1 | 7/2006 | Schwammenthal et al. |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0229719 A1 | 10/2006 | Marquez et al. |
| 2006/0235508 A1 | 10/2006 | Lane et al. |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2006/0293745 A1 | 12/2006 | Carpentier et al. |
| 2007/0005129 A1 | 1/2007 | Damm et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016287 A1 | 1/2007 | Cartledge et al. |
| 2007/0016288 A1 | 1/2007 | Gurskis et al. |
| 2007/0043435 A1 | 2/2007 | Seguin et al. |
| 2007/0067029 A1 | 3/2007 | Gabbay |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0100441 A1 | 5/2007 | Kron et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244546 A1 | 10/2007 | Francis |
| 2007/0244558 A1 | 10/2007 | Machiraju |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0021546 A1 | 1/2008 | Patz et al. |
| 2008/0027483 A1 | 1/2008 | Cartledge et al. |
| 2008/0033543 A1 | 2/2008 | Gurskis et al. |
| 2008/0065198 A1 | 3/2008 | Quintessenza |
| 2008/0114452 A1 | 5/2008 | Gabbay |
| 2008/0119875 A1 | 5/2008 | Ino et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |

(56) References Cited

U.S. PATENT DOCUMENTS

| | | |
|---|---|---|
| 2008/0183273 A1 | 7/2008 | Mesana et al. |
| 2008/0188929 A1 | 8/2008 | Schreck |
| 2008/0200980 A1 | 8/2008 | Robin et al. |
| 2008/0208327 A1 | 8/2008 | Rowe |
| 2008/0208329 A1 | 8/2008 | Bishop et al. |
| 2008/0215144 A1 | 9/2008 | Ryan et al. |
| 2008/0228263 A1 | 9/2008 | Ryan |
| 2008/0243246 A1 | 10/2008 | Ryan et al. |
| 2008/0269878 A1 | 10/2008 | Iobbi |
| 2008/0275549 A1 | 11/2008 | Rowe |
| 2008/0281411 A1 | 11/2008 | Berreklouw |
| 2008/0319543 A1 | 12/2008 | Lane |
| 2009/0005863 A1 | 1/2009 | Goetz et al. |
| 2009/0036903 A1 | 2/2009 | Ino et al. |
| 2009/0082857 A1 | 3/2009 | Lashinski et al. |
| 2009/0093876 A1 | 4/2009 | Nitzan et al. |
| 2009/0192591 A1 | 7/2009 | Ryan et al. |
| 2009/0192599 A1 | 7/2009 | Lane et al. |
| 2009/0192602 A1 | 7/2009 | Kuehn |
| 2009/0192603 A1 | 7/2009 | Kuehn |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0216322 A1 | 8/2009 | Le et al. |
| 2009/0281609 A1 | 11/2009 | Benichou et al. |
| 2010/0076548 A1 | 3/2010 | Konno |
| 2010/0076549 A1 | 3/2010 | Keidar et al. |
| 2010/0145438 A1 | 6/2010 | Barone |
| 2010/0161036 A1 | 6/2010 | Pintor et al. |
| 2010/0249894 A1 | 9/2010 | Oba et al. |
| 2010/0249908 A1 | 9/2010 | Chau et al. |
| 2010/0256723 A1 | 10/2010 | Murray |
| 2010/0331972 A1 | 12/2010 | Pintor et al. |
| 2011/0022165 A1 | 1/2011 | Oba et al. |
| 2011/0147251 A1 | 6/2011 | Hodshon et al. |
| 2011/0166636 A1 | 7/2011 | Rowe |
| 2011/0178597 A9 | 7/2011 | Navia et al. |
| 2011/0264207 A1 | 10/2011 | Bonhoeffer et al. |
| 2011/0276128 A1 | 11/2011 | Cao et al. |
| 2012/0046738 A1 | 2/2012 | Lau et al. |
| 2012/0065729 A1 | 3/2012 | Pintor et al. |
| 2012/0078357 A1 | 3/2012 | Conklin |
| 2012/0101570 A1 | 4/2012 | Tuval et al. |
| 2012/0150288 A1 | 6/2012 | Hodshon et al. |
| 2012/0165928 A1 | 6/2012 | Nitzan et al. |
| 2012/0226348 A1 | 9/2012 | Lane et al. |
| 2013/0053949 A1 | 2/2013 | Pintor et al. |
| 2013/0090725 A1 | 4/2013 | Pintor et al. |
| 2013/0116777 A1 | 5/2013 | Pintor et al. |
| 2013/0190862 A1 | 7/2013 | Pintor et al. |
| 2014/0188219 A1 | 7/2014 | Conklin et al. |
| 2014/0188221 A1 | 7/2014 | Chung et al. |
| 2015/0366664 A1 | 12/2015 | Guttenberg et al. |
| 2017/0000603 A1 | 1/2017 | Conklin et al. |
| 2017/0000604 A1 | 1/2017 | Conklin et al. |
| 2017/0172739 A1 | 6/2017 | Chang et al. |
| 2018/0206986 A1 | 7/2018 | Noe et al. |
| 2018/0289475 A1 | 10/2018 | Chung et al. |
| 2019/0142584 A1 * | 5/2019 | Braido ............... A61F 2/2418 623/1.26 |
| 2020/0383779 A1 | 12/2020 | Conklin et al. |

FOREIGN PATENT DOCUMENTS

| | | |
|---|---|---|
| EP | 0143246 A2 | 6/1985 |
| EP | 0338994 A1 | 10/1989 |
| EP | 1034753 A1 | 9/2000 |
| EP | 1755459 | 2/2007 |
| EP | 1804726 | 7/2007 |
| EP | 1958598 A1 | 8/2008 |
| WO | 9213502 A1 | 8/1992 |
| WO | 9742871 A1 | 11/1997 |
| WO | 2012047644 A2 | 4/2012 |
| WO | 2013096854 A2 | 6/2013 |
| WO | 2015196152 A1 | 12/2015 |

OTHER PUBLICATIONS

Sadowski, Jerzy; Kapelak, Boguslaw; Bartus, Krzysztof, "Sutureless Heart Valve Implantation—A Case Study," Touch Briefings, 2005, pp. 48-50.

* cited by examiner

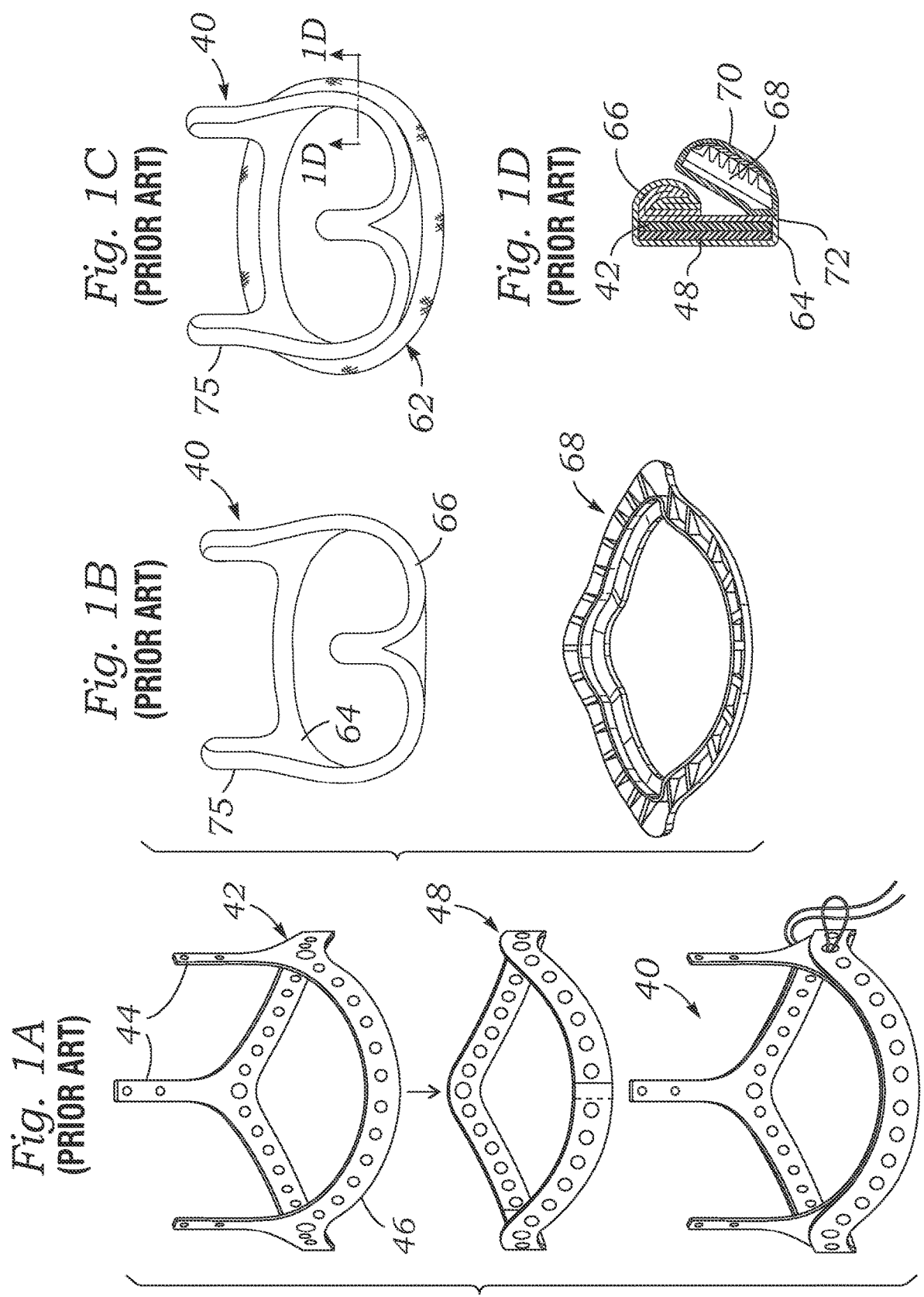

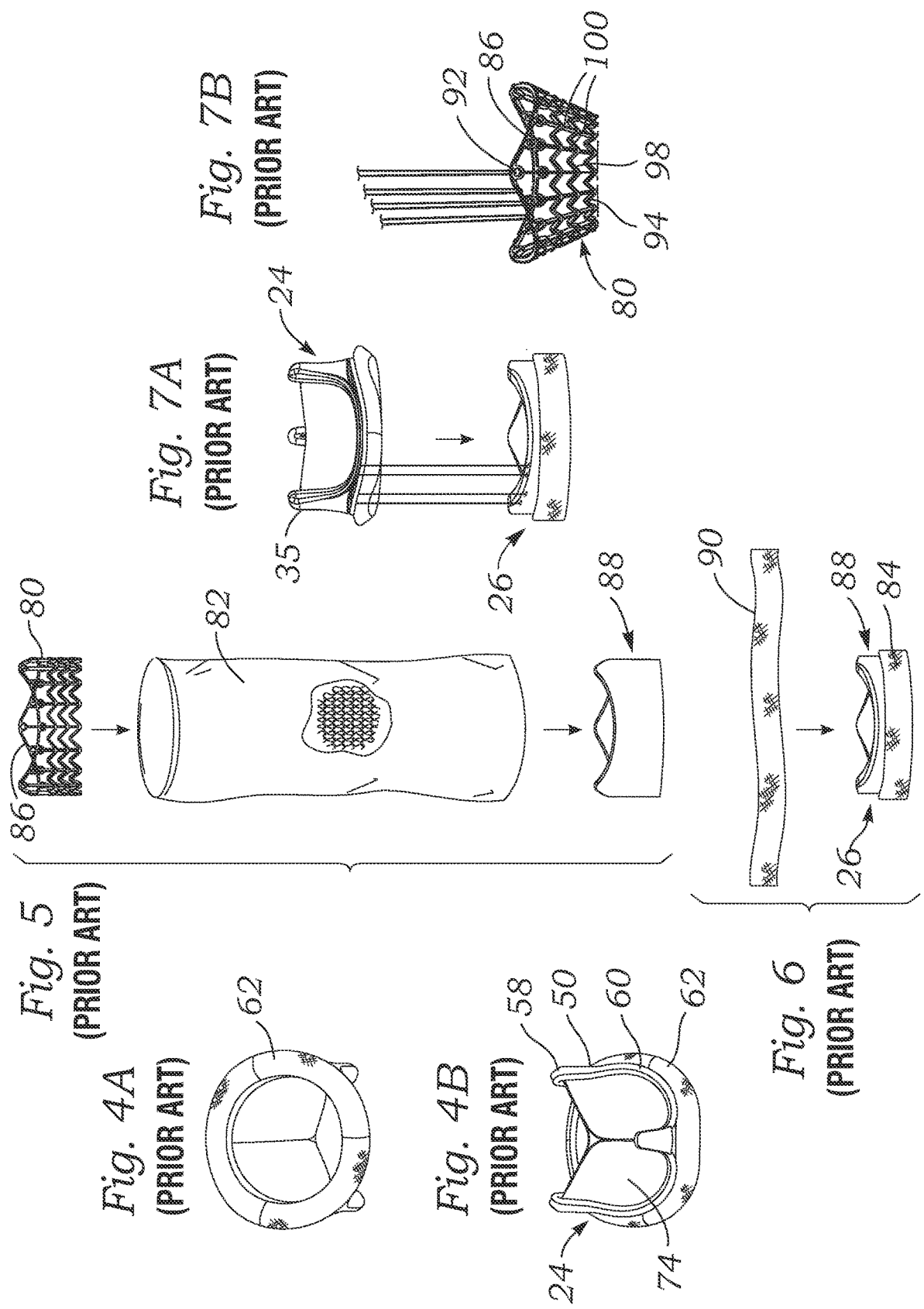

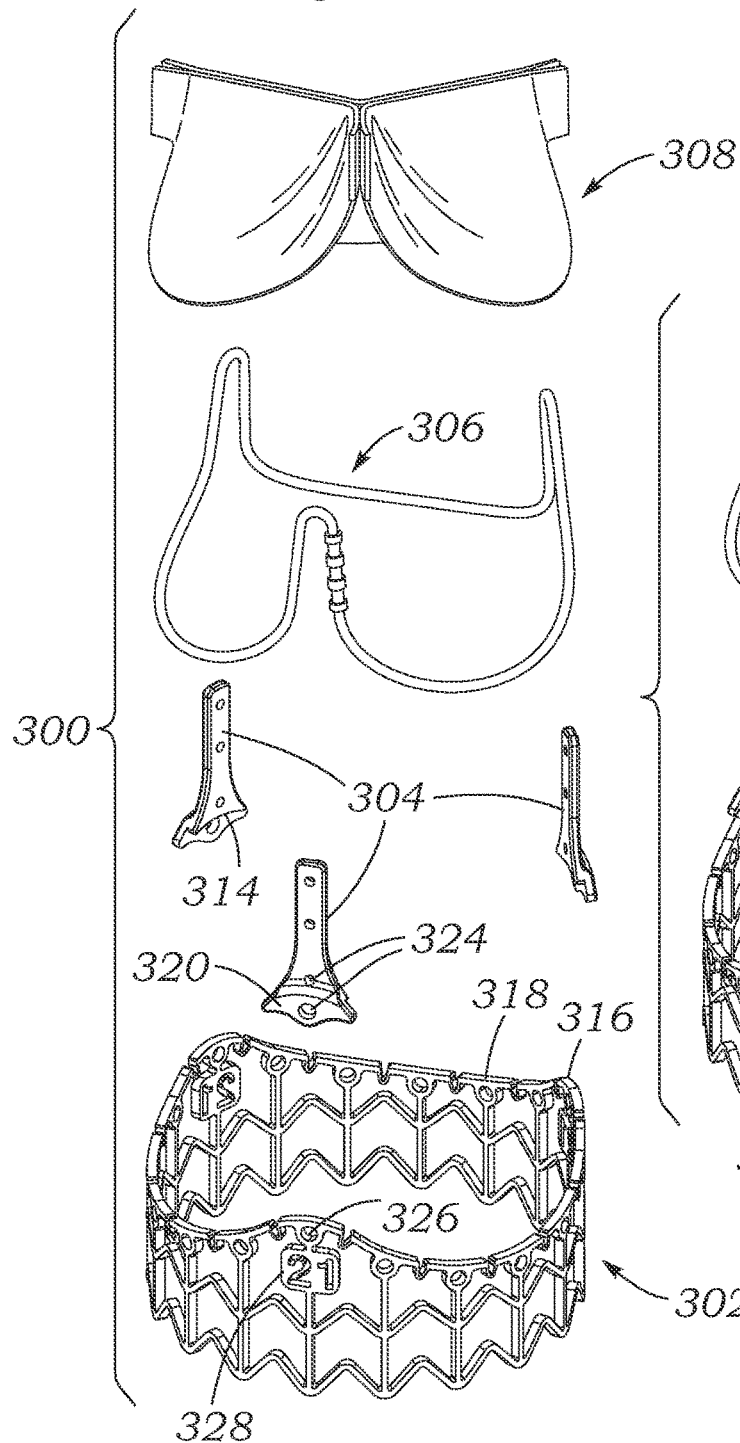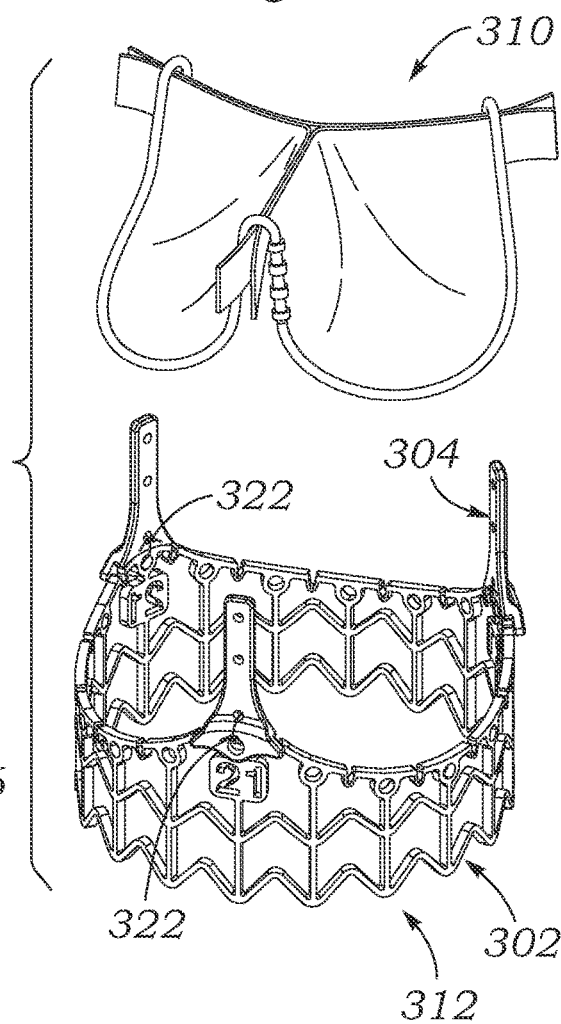

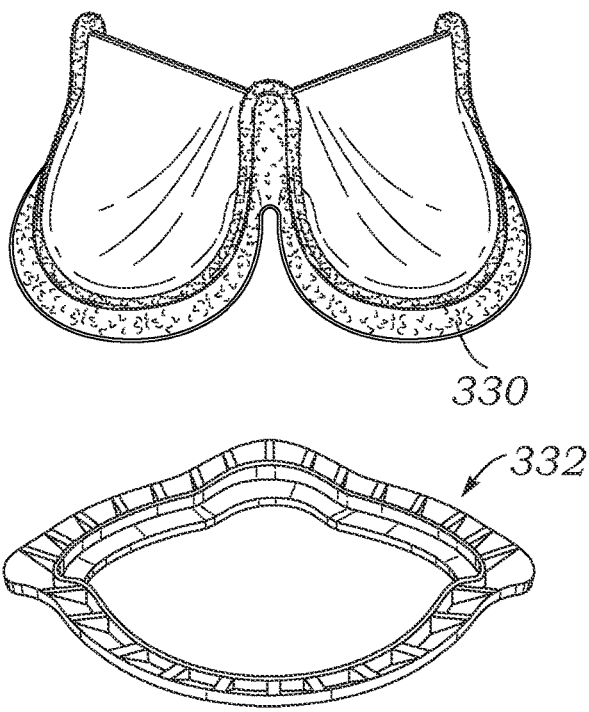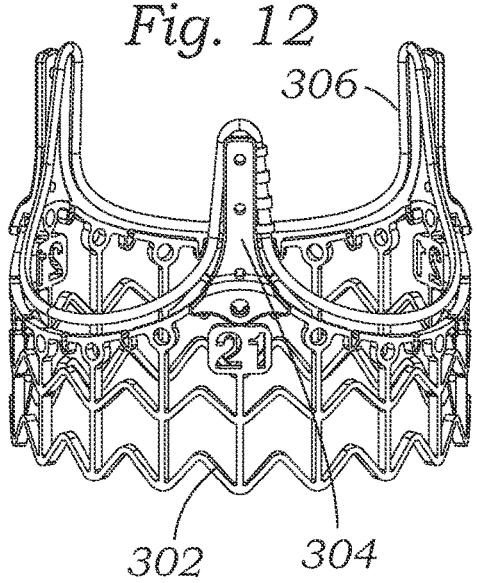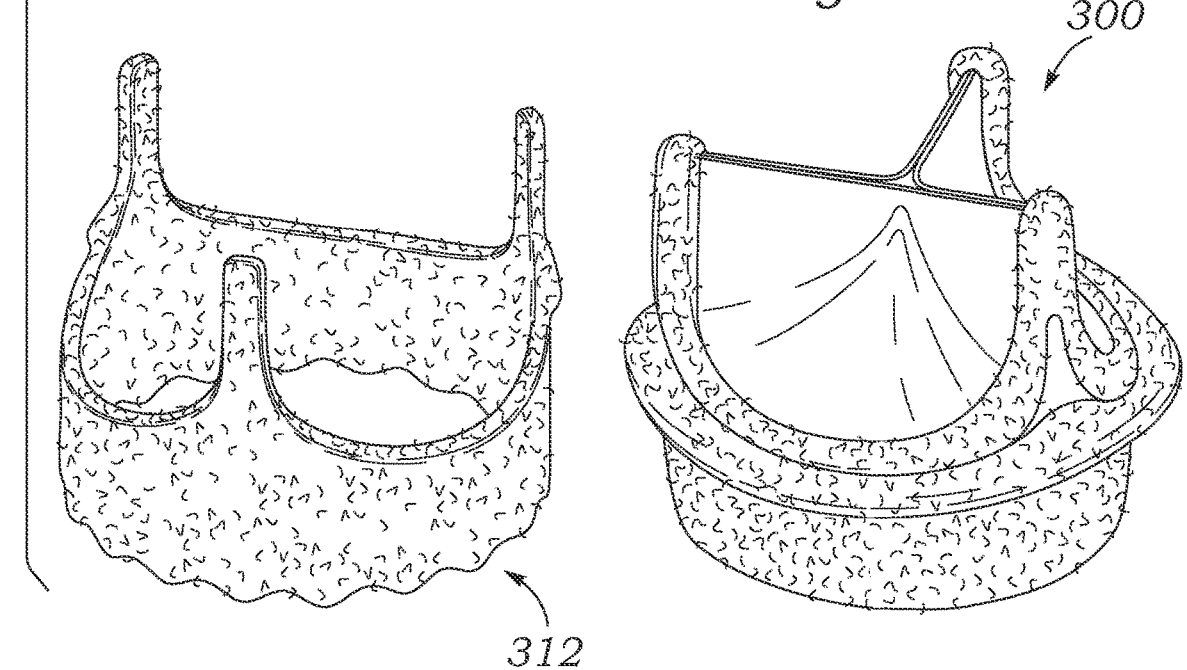

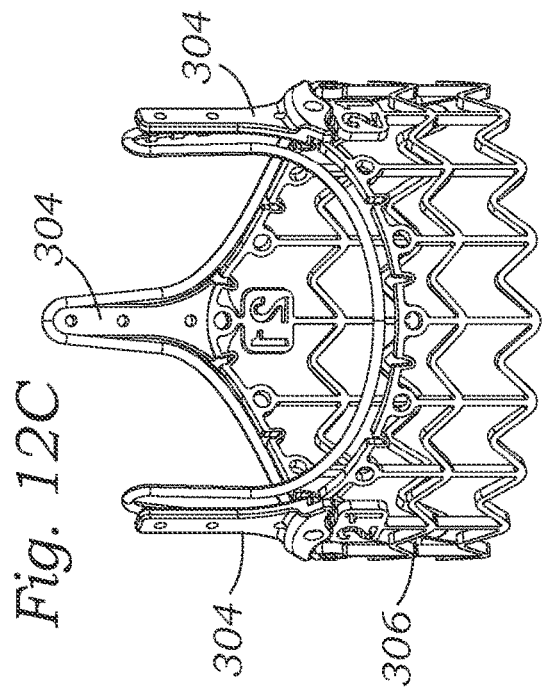
Fig. 12C
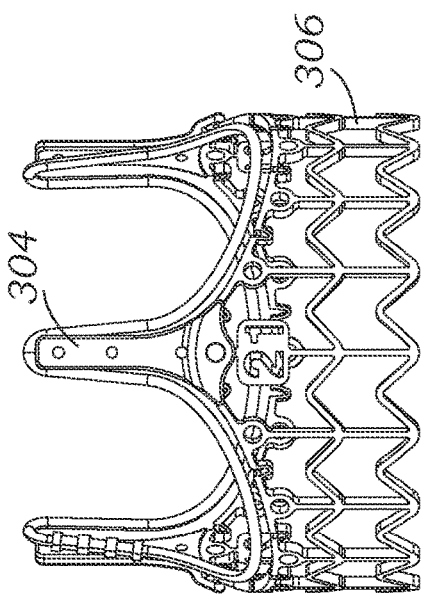
Fig. 12D
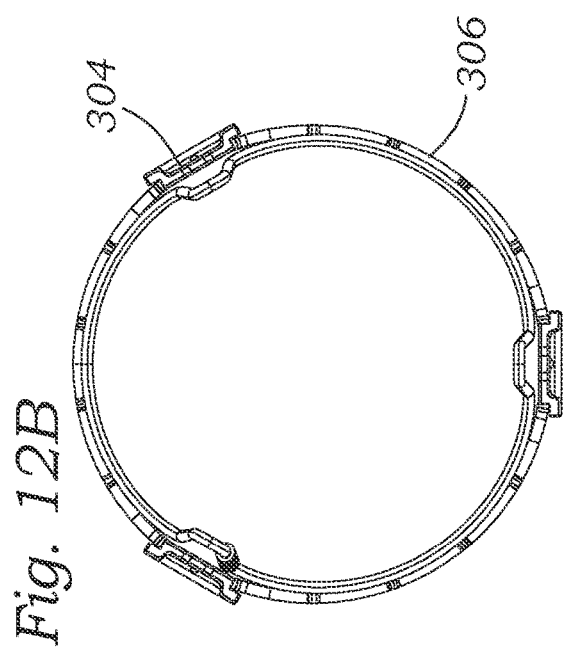
Fig. 12B
Fig. 12A

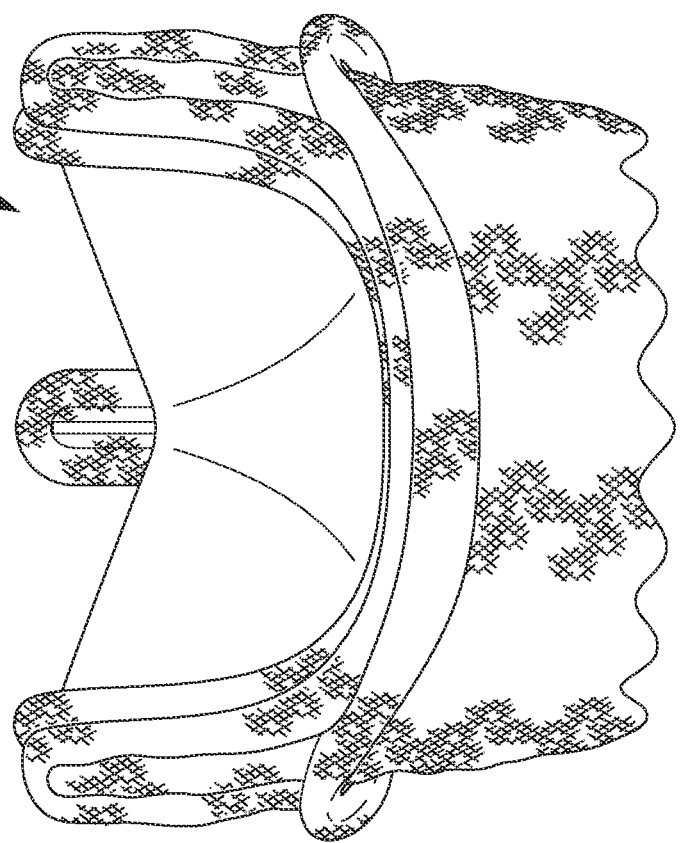
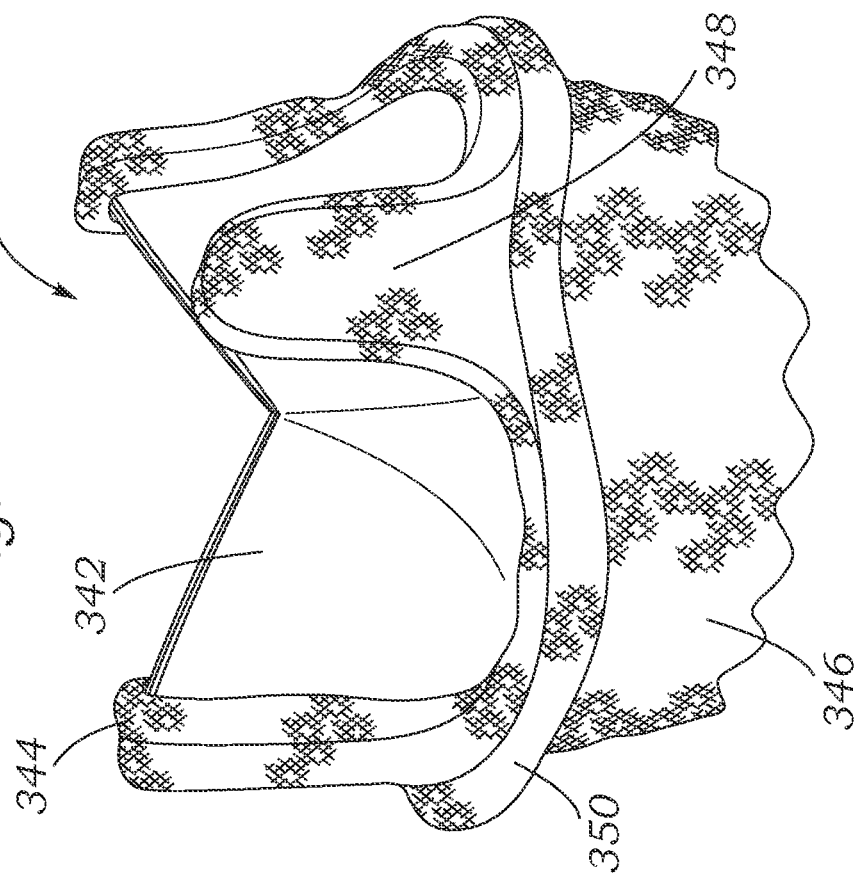

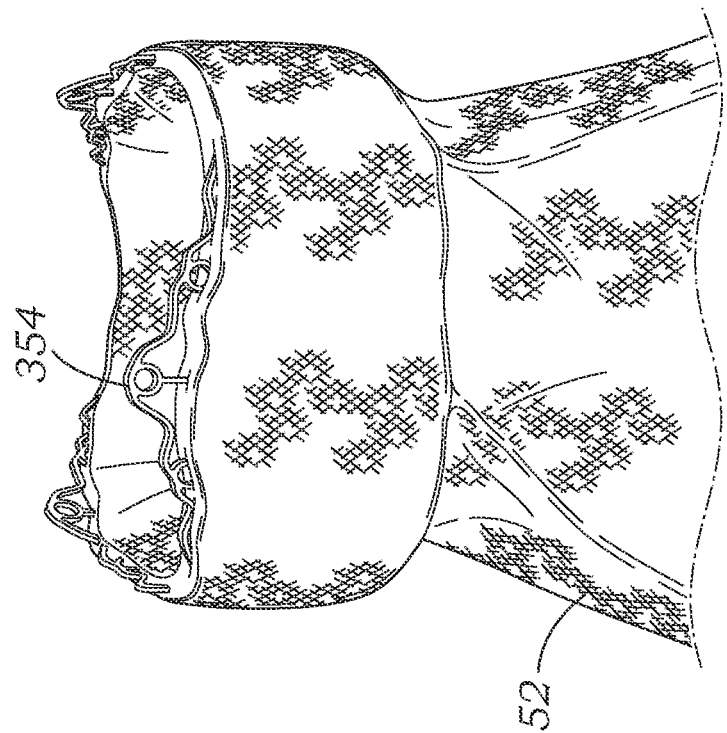
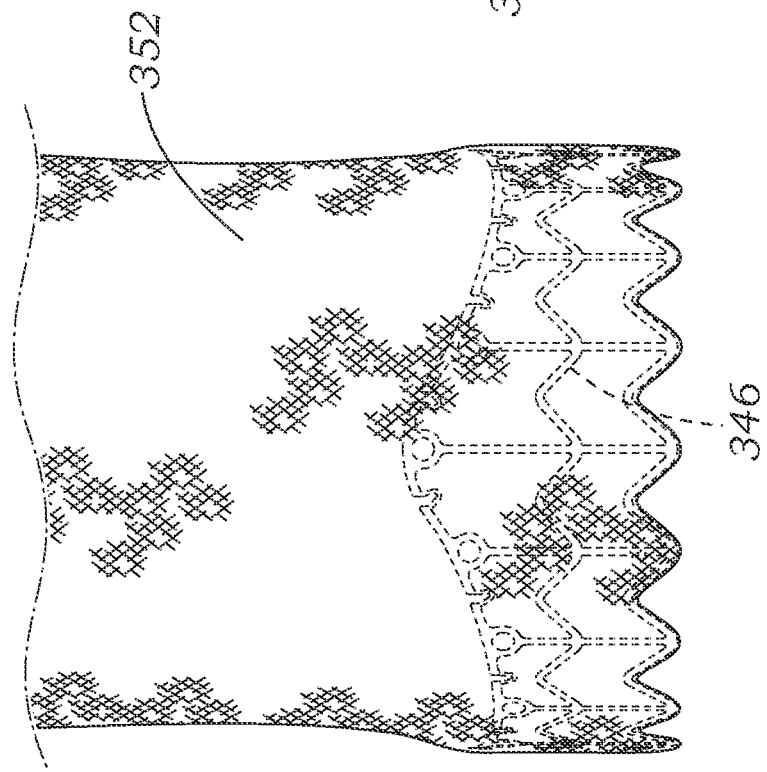

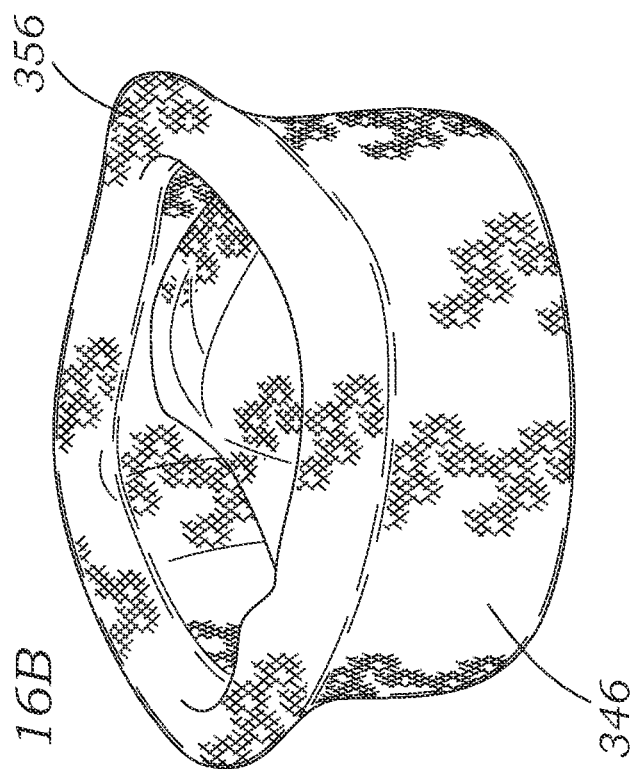
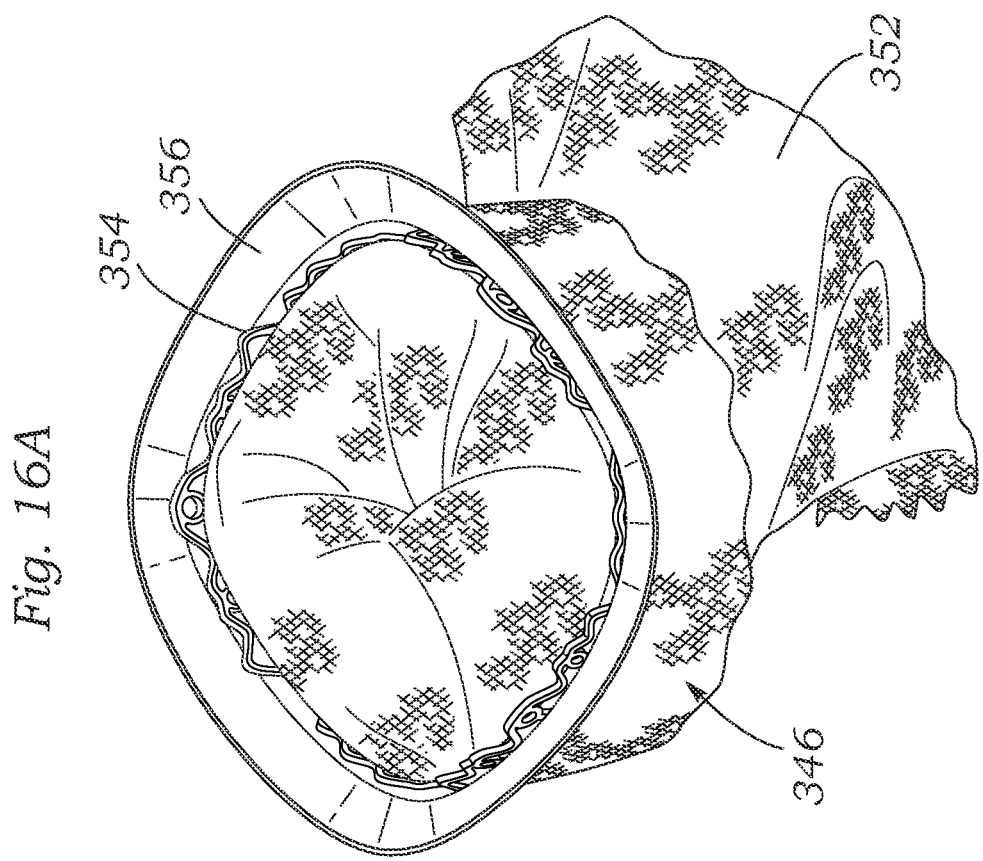

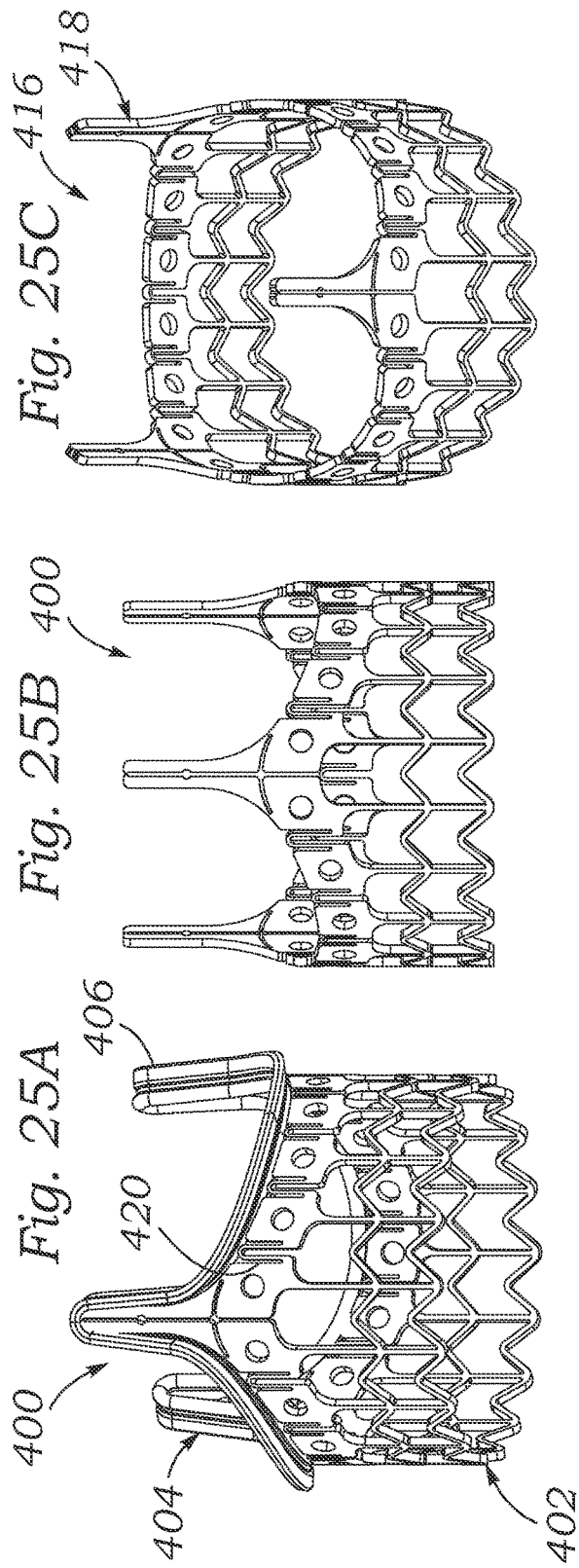

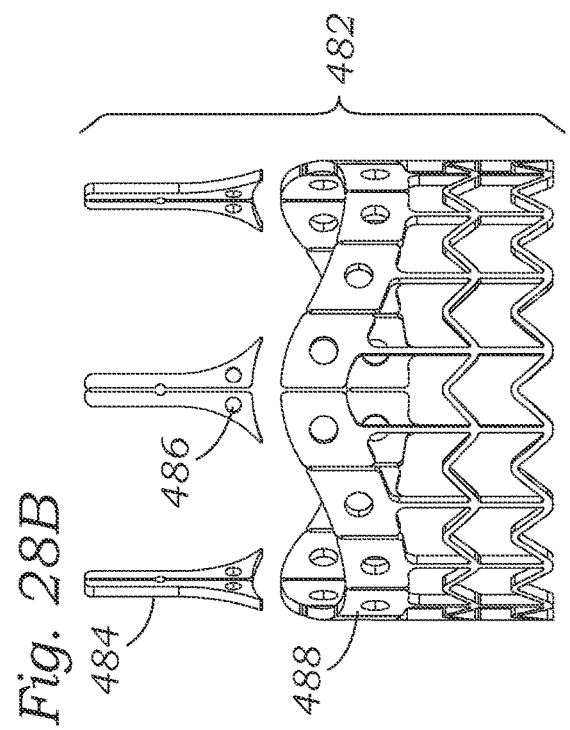
Fig. 28A
Fig. 28B
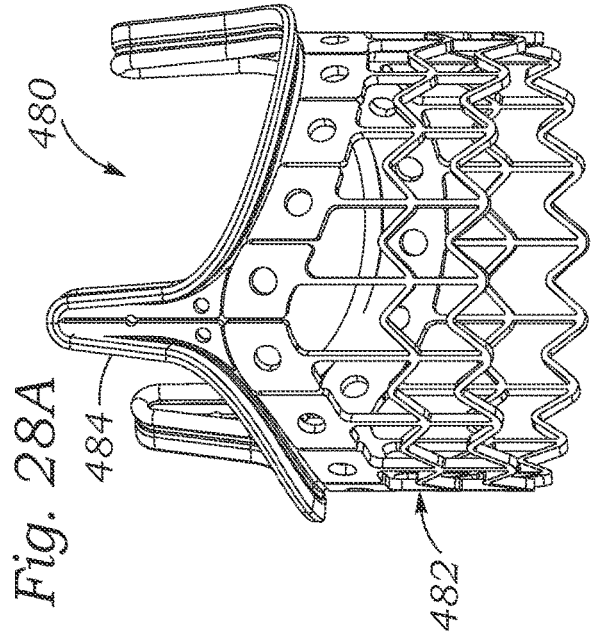
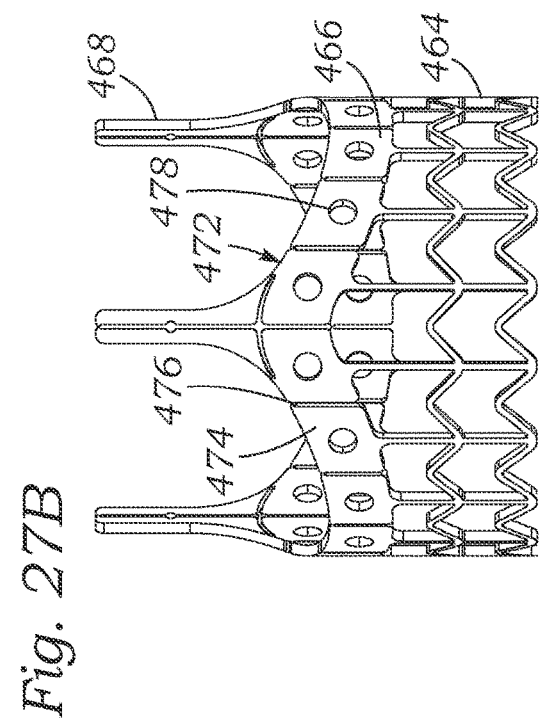
Fig. 27A
Fig. 27B
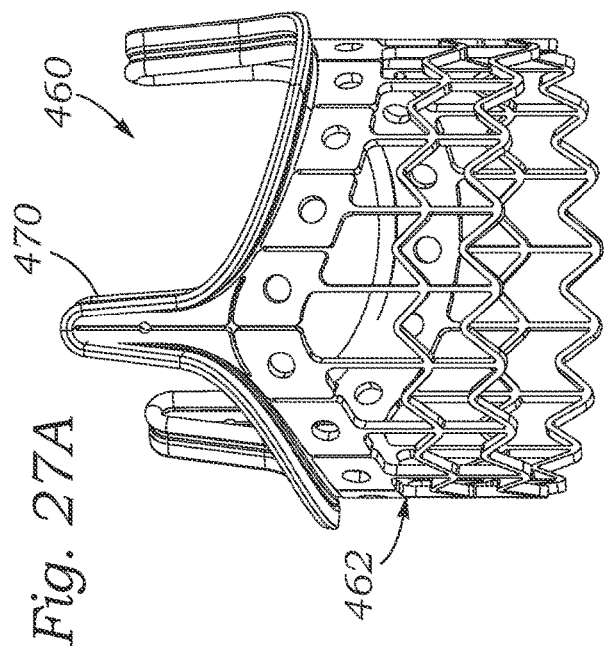

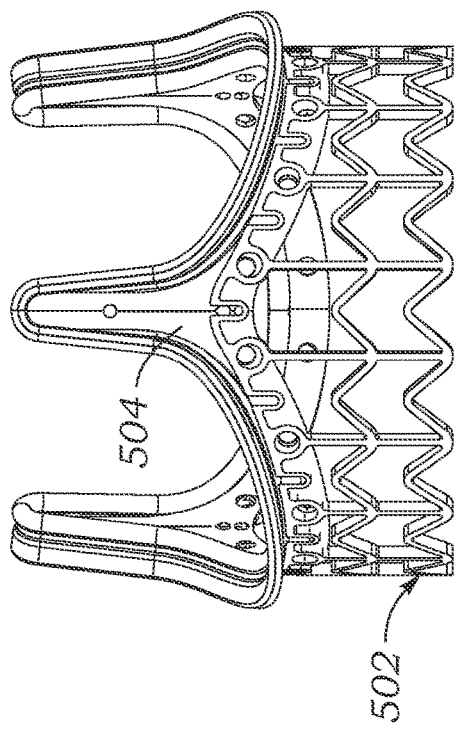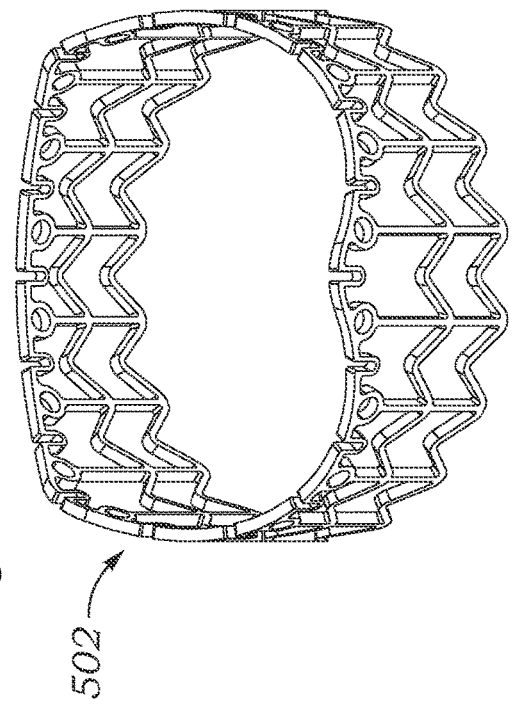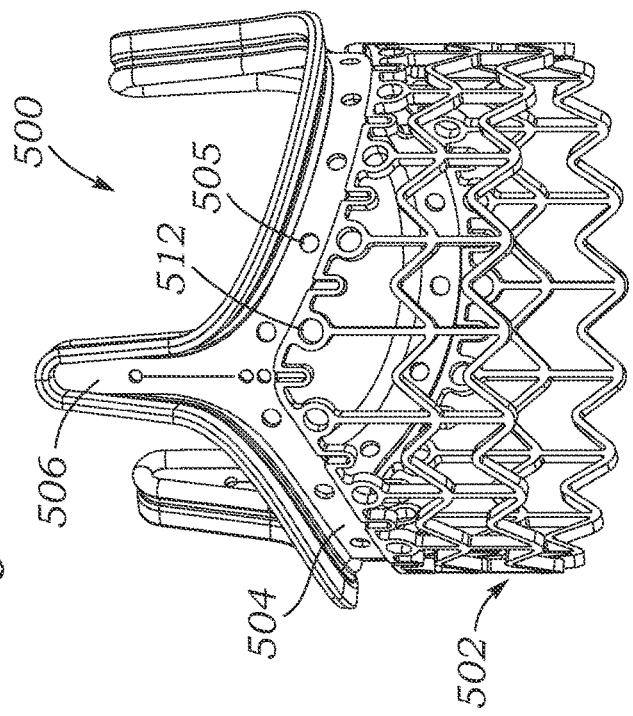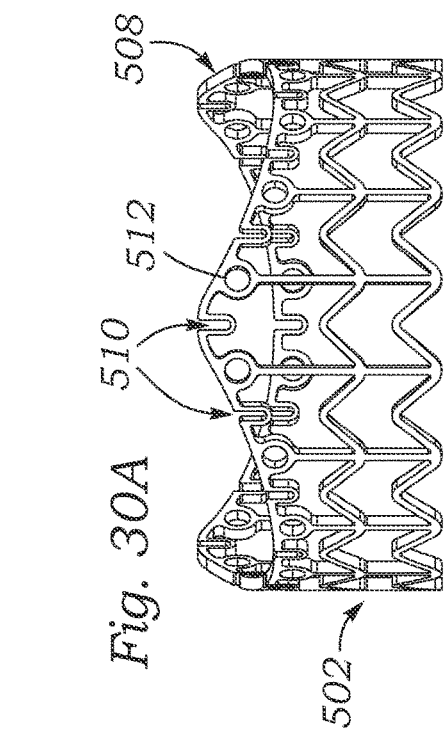

HYBRID HEART VALVES

CROSS REFERENCE TO RELATED APPLICATIONS

This application is a continuation of U.S. application Ser. No. 16/666,331, filed Oct. 28, 2019, now U.S. Pat. No. 11,654,020, which is a continuation of U.S. application Ser. No. 15/199,748, filed Jun. 30, 2016, now U.S. Pat. No. 10,456,246, which claims the benefit of U.S. Application No. 62/188,465, filed Jul. 2, 2015, the entire disclosures all of which are incorporated by reference. This application is related to U.S. Patent Application 62/188,467, filed Jul. 2, 2015, titled "HYBRID HEART VALVES ADAPTED FOR POST-IMPLANT EXPANSION", the entire disclosure which is incorporated by reference.

TECHNICAL FIELD

The present disclosure relates to a hybrid heart valve for heart valve replacement, and more particularly to modifications to simplify the construction of hybrid heart valves.

BACKGROUND

The heart is a hollow muscular organ having four pumping chambers separated by four heart valves: aortic, mitral (or bicuspid), tricuspid, and pulmonary. Heart valves are comprised of a dense fibrous ring known as the annulus, and leaflets or cusps attached to the annulus.

Heart valve disease is a widespread condition in which one or more of the valves of the heart fails to function properly. In a traditional valve replacement operation, the damaged leaflets are typically excised and the annulus sculpted to receive a replacement prosthetic valve.

In tissue-type valves, a whole xenograft valve (e.g., porcine) or a plurality of xenograft leaflets (e.g., bovine pericardium) can provide fluid occluding surfaces. Synthetic leaflets have been proposed, and thus the term "flexible leaflet valve" refers to both natural and artificial "tissue-type" valves. In a typical tissue-type valve, two or more flexible leaflets are mounted within a peripheral support structure that usually includes posts or commissures extending in the outflow direction to mimic natural fibrous commissures in the native annulus. The metallic or polymeric "support frame," sometimes called a "wireform" or "stent," has a plurality (typically three) of large radius cusps supporting the cusp region of the flexible leaflets (e.g., either a whole xenograft valve or three separate leaflets). The ends of each pair of adjacent cusps converge somewhat asymptotically to form upstanding commissures that terminate in tips, each extending in the opposite direction as the arcuate cusps and having a relatively smaller radius. Components of the valve are usually assembled with one or more biocompatible fabrics (e.g., polyester, for example, Dacron® polyethylene terephthalate (PET)) coverings, and a fabric-covered sewing ring is provided on the inflow end of the peripheral support structure.

There is a need for a prosthetic valve that can be surgically implanted in a body channel in a more efficient procedure so as to reduce the time required on extracorporeal circulation. One solution especially for aortic valve replacement is provided by the Edwards Intuity® valve system available from Edwards Lifesciences of Irvine, CA. Aspects of the Edwards Intuity® valve system are disclosed in U.S. Pat. No. 8,641,757 to Pintor, et al. The Edwards Intuity® valve is a hybrid of a surgical valve and a plastically-expandable stent that helps secure the valve in place in a shorter amount of time.

Despite certain advances in this area, there remains a need for a simplified prosthetic heart valve that facilitates implant and simplifies manufacturing techniques.

SUMMARY

The application discloses a hybrid prosthetic heart valve (and methods for making the same) having a stent frame positioned at the inflow end of the prosthetic heart valve configured to plastically expand into a substantially flared shape when subjected to a dilation force that is by itself insufficient to cause expansion of the main support structure. The stent frame is positioned upstream or on the inflow end of the entire valve portion. The application also discloses a hybrid prosthetic heart valve configured to receive a prosthetic heart valve, such as a catheter-deployed (transcatheter) prosthetic heart valve, therein—e.g., it is adapted for valve-in-valve (ViV) procedures.

An exemplary hybrid prosthetic heart valve having an inflow end and an outflow end, and comprises a valve member including a plurality of flexible leaflets configured to ensure one-way blood flow therethrough. A generally tubular expandable inflow stent frame having a radially-expandable inflow end and an outflow end is secured to and projects from an inflow end of the valve member. The outflow end of the stent frame undulates with peaks and valleys, and the outflow end includes integrated commissure posts to which the leaflets attach. The outflow end of the stent frame has a circumferential structure defining a nominal diameter that enables physiological functioning of the valve member when implanted. The circumferential structure is radially expandable from the nominal diameter to a larger expanded diameter upon application of an outward dilatory force from within the stent frame substantially larger than forces associated with normal physiological use. And the circumferential structure has limited radially compressibility of between about 7-20% of the nominal diameter to reduce the size of the outflow end during delivery of the heart valve.

A further hybrid prosthetic heart valve disclosed herein and adapted for post-implant expansion has an inflow end and an outflow end with a valve member and an inflow stent frame. The valve member includes an undulating wireform supporting a plurality of flexible leaflets configured to ensure one-way blood flow therethrough. The stent frame is plastically-expandable with a radially-expandable inflow end and an outflow end secured to an inflow end of the wireform. The stent frame projects from the inflow end of the wireform and the outflow end undulates with peaks and valleys corresponding to the wireform. The outflow end further includes integrated commissure posts to which the leaflets attach, and defines an implant circumference that is non-compressible in normal physiological use and has a nominal diameter. The stent frame outflow end permits expansion from the nominal diameter to a second diameter larger than the nominal diameter upon application of an outward dilatory force from within the outflow end substantially larger than forces associated with normal physiological use.

Another hybrid prosthetic heart valve disclosed herein comprises a valve member including an undulating wireform supporting a plurality of flexible leaflets configured to ensure one-way blood flow therethrough. A plastically-expandable inflow stent frame having a radially-expandable inflow end and an outflow end is secured to an inflow end of the wireform. The stent frame projects from the inflow end of the wireform and the outflow end undulates with peaks and valleys corresponding to the wireform. The outflow end includes integrated commissure posts to which the leaflets attach outside of the wireform, and the outflow end comprises a circumferential structure defining a nominal diameter that enables functioning of the valve member. The circumferential structure is radially compressible to a smaller contracted diameter to enable compression of the outflow end during delivery of the heart valve, and radially expandable from the nominal diameter to a larger expanded diameter upon application of an outward dilatory force from within the stent frame substantially larger than forces associated with normal physiological use.

Other features and advantages of the present invention will become apparent from the following detailed description, taken in conjunction with the accompanying drawings that illustrate, by way of example, the principles of the invention.

BRIEF DESCRIPTION OF THE DRAWINGS

FIG. 1A is an exploded view of an inner structural band subassembly of a prior art prosthetic heart valve, and FIG. 1B shows the band subassembly having been covered with cloth and exploded over a peripheral sealing ring;

FIG. 1C shows the cloth-covered band subassembly joined with the peripheral sealing ring also covered in cloth, while FIG. 1D is a vertical sectional view through a cusp region thereof;

FIGS. 4A and 4B are inflow and outflow perspective views, respectively, of a prosthetic heart valve as in FIG. 3 before coupling with an inflow anchoring skirt to form a hybrid prosthetic heart valve;

FIG. 5 is an exploded assembly view of a portion of a cloth-covered anchoring skirt for coupling to the heart valve;

FIG. 6 is an exploded assembly view of the portion of the cloth-covered anchoring skirt shown in FIG. 5 and a lower sealing flange secured thereto to form the inflow anchoring skirt;

FIG. 7A shows the valve member above the cloth-covered anchoring skirt and schematically shows one method of coupling the two elements, while FIG. 7B illustrates an inner plastically-expandable stent frame of the anchoring skirt and the pattern of coupling sutures passed therethrough;

FIG. 8A is a side view of a hybrid prosthetic heart valve of the present application, while

FIG. 10A is an exploded perspective view of components of an alternative hybrid prosthetic heart valve, while FIG. 10B shows an exemplary leaflet and wireform subassembly and an anchoring skirt and commissure post subassembly for the hybrid prosthetic heart valve;

FIG. 11 is another exploded perspective view of subassemblies of the alternative hybrid prosthetic heart valve;

FIG. 12 shows the relative positions of the anchoring skirt and commissure post subassembly and wireform for the alternative hybrid prosthetic heart valve, and FIGS. 12A-12D are further detailed views thereof;

FIG. 13 is a perspective view of the finished hybrid prosthetic heart valve;

FIGS. 14A and 14B are perspective views of a hybrid prosthetic heart valve built using the methods of FIGS. 15-16;

FIGS. 15A and 15B show steps for covering an anchoring frame member with cloth in the disclosed method of hybrid valve construction;

FIGS. 16A and 16B show methods of attachment of a suture permeable sealing ring to the anchoring frame member;

FIGS. 25A-25D are perspective, elevational, and flat plan views of an exemplary integrated frame member for use in the hybrid prosthetic heart valves disclosed herein;

FIGS. 27A and 27B are perspective and elevational views of a still further integrated frame member of the present application that is non-collapsible and non-expandable;

FIGS. 28A and 28B are perspective and elevational views of another integrated frame member with separate commissure posts;

FIG. 29 is a perspective view of an alternative integrated frame member having an expandable frame connected to a polymer band that forms commissure posts;

FIGS. 30A and 30B are elevational and perspective views of an exemplary expandable frame for use in the frame member of FIG. 29; and FIG. 31 is an elevational view of an integrated frame member similar to that shown in FIG. 29 with the polymer band overlapping an upper edge of the expandable frame.

DETAILED DESCRIPTION OF CERTAIN EMBODIMENTS

Figure 2A:
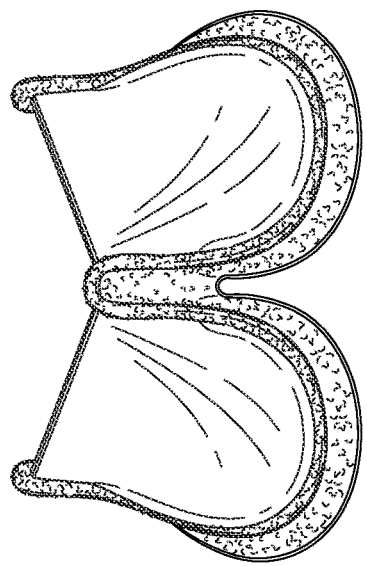
FIG. 2A is a perspective view of a flexible leaflet subassembly for use in the prior art prosthetic heart valve.

The prosthetic heart valves disclosed herein are "hybrid" in that they include a prosthetic valve member with a relatively stable diameter, and a lower expandable frame structure to help in anchoring the valve in place. Most prior valves have either a wholly non-compressible/non-expandable valve member or a wholly expandable frame structure that incorporates a valve therein. One specific commercial prosthetic heart valve that is constructed in a hybrid manner is the Edwards Intuity® valve system from Edwards Lifesciences of Irvine, CA. The hybrid Edwards Intuity® valve system comprises a surgical non-compressible/non-expandable valve member (e.g., Edwards Magna Ease® valve) having bioprosthetic (e.g., bovine pericardial) leaflets coupled to a stainless steel expandable frame structure on its inflow end.

FIGS. 1-7 illustrate a number of steps in the construction of an exemplary hybrid prosthetic heart valve 20.

FIG. 1A is an exploded view of an inner structural band subassembly 40, and FIG. 1B shows the band subassembly having been covered with cloth and exploded over a peripheral sealing ring. The inner structural band subassembly 40 includes an inner polymer band 42 having three upstanding posts 44 and a scalloped lower ring 46, and an outer more rigid band 48 having a scalloped shape to conform to the lower ring 46. The band subassembly 40 is formed by positioning the polymer band 42 within the rigid band 48 and securing them together with sutures through aligned holes, for example.

FIG. 1B is a perspective view of the assembled band subassembly 40 covered in cloth exploded from a sewing ring 68. The two structural bands 42, 48 are the same heights in the cusp region and encompassed by a fabric cover 64 that is rolled into a peripheral tab 66. As seen in FIG. 1D, the sewing ring 62 comprises an inner suture permeable member 68 having a frustoconical form and encompassed by a second fabric cover 70. Two fabric covers 64, 70 are sewn together at a lower junction point 72 to form the cloth-covered assembly of FIG. 1C, while FIG. 1D shows details through a cusp portion thereof.

Figure 2C:
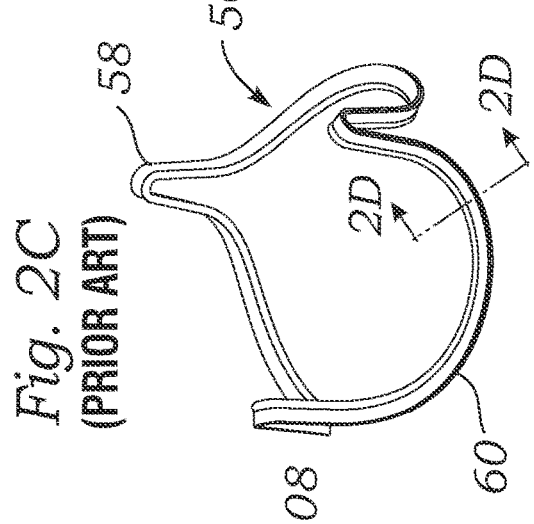
FIG. 2C is a perspective view of a subassembly of the undulating wireform covered in fabric.
Figure 2E:
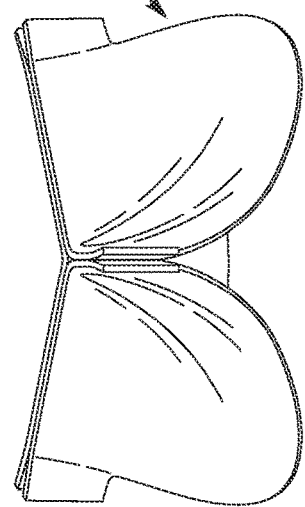
FIG. 2E shows a leaflet and wireform subassembly for prior art prosthetic heart valves.
Figure 2B:
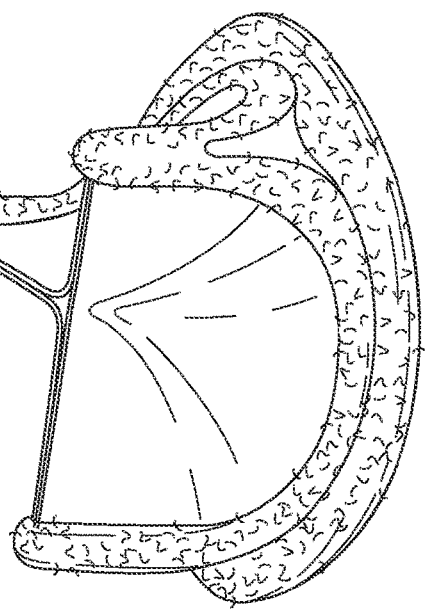
FIG. 2B shows an undulating wireform used for support thereof.
Figure 2D:
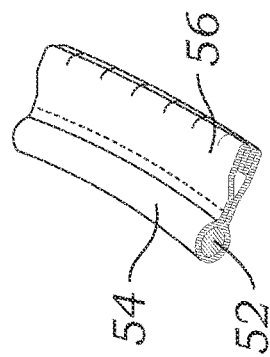
FIG. 2D is a detailed sectional view of a cusp portion thereof.

FIG. 2A is a perspective view of a flexible leaflet subassembly and FIG. 2B shows an undulating wireform used for support thereof. FIG. 2C is a perspective view of a cloth-covered wireform subassembly 50, and FIG. 2D is a detailed sectional view of a cusp portion of the wireform 50 showing an inner wire member 52 covered with fabric that defines a tubular portion 54 and an outwardly projecting flap 56. The wireform 50 defines three upstanding commissure posts 58 and three downwardly convex cusps 60. This is a standard shape for tri-leaflet heart valves and mimics the peripheral edges of the three native aortic leaflets. The shape of the wireform 50 coincides with the upper edge of the band subassembly 40, and defines the outflow edge of the prosthetic valve 20. The wireform subassembly 50 is then joined together with the flexible leaflet subassembly, as seen in FIG. 2E.

Figure 3:
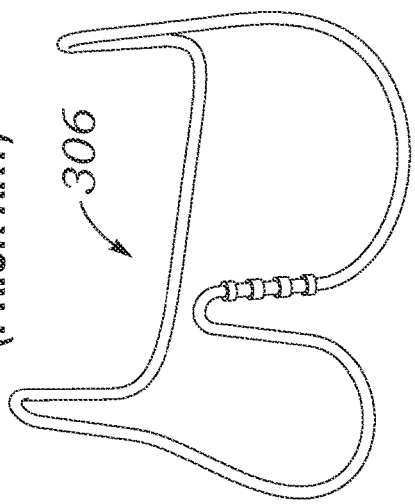
FIG. 3 is a perspective view of a finished prior art prosthetic heart valve including the combination of the subassemblies shown in FIGS. 1C and 2E.

FIG. 3 is a perspective view of a finished valve member including the combination of the subassemblies shown in FIGS. 1C and 2E.

FIGS. 4A and 4B are inflow and outflow perspective views, respectively, of the surgical heart valve member 24 before coupling with an inflow anchoring skirt to form the hybrid heart valve 20. Although construction details are not shown, three flexible leaflets 74 are secured along the undulating wireform 50 and then to the combination of the band subassembly 40 and sewing ring 62 shown in FIG. 1C. In a preferred embodiment, each of the three leaflets includes outwardly projecting tabs that pass through the inverted U-shaped commissure posts 58 and wrap around the cloth-covered commissure posts 75 (see FIG. 1C) of the band subassembly 40. The entire structure at the commissures is covered with a secondary fabric to form the valve commissures 35 as seen in FIG. 7A.

One feature of the valve member 24 that is considered particularly important is the sewing ring 62 that surrounds the inflow end thereof. As will be seen, the sewing ring 62 is used to attach the anchoring skirt 26 to the valve member 24. Moreover, the sewing ring 62 presents an outward flange that contacts an atrial side of the annulus, while the anchoring skirt 26 expands and contracts the opposite, ventricular side of the annulus, therefore securing the heart valve 20 to the annulus from both sides. Furthermore, the presence of the sewing ring 62 provides an opportunity for the surgeon to use conventional sutures to secure the heart valve 20 to the annulus as a contingency.

The preferred sewing ring 62 defines a relatively planar upper or outflow face and an undulating lower face. Cusps of the valve structure abut the sewing ring upper face opposite locations where the lower face defines peaks. Conversely, the valve commissure posts align with locations where the sewing ring lower face defines troughs. The undulating shape of the lower face advantageously matches the anatomical contours of the aortic side of the annulus AA, that is, the supra-annular shelf. The ring 62 preferably comprises a suture-permeable material such as rolled synthetic fabric or a silicone inner core covered by a synthetic fabric. In the latter case, the silicone may be molded to define the contour of the lower face and the fabric cover conforms thereover.

Now with reference to FIGS. 5 and 6, assembly of the cloth-covered anchoring skirt 26 will be described. FIG. 5 is an exploded assembly view of a portion of a cloth-covered anchoring skirt for coupling to the valve member, and FIG. 6 is an exploded assembly view of the portion of the cloth-covered anchoring skirt shown in FIG. 5 and a lower sealing flange secured thereto to form the inflow anchoring skirt. It should first be noted that the size of the anchoring skirt 26 will vary depending on the overall size of the heart valve 20. Therefore the following discussion applies to all sizes of valve components, with the dimensions scaled accordingly.

The general function of the anchoring skirt 26 is to provide the means to attach the prosthetic valve member 24 to the native aortic root. The anchoring skirt 26 may be a pre-crimped, tapered, 316L stainless steel balloon-expandable stent, desirably covered by a polyester fabric to help seal against paravalvular leakage and to promote tissue ingrowth once implanted within the annulus. The anchoring skirt 26 transitions between the tapered, constricted shape of FIG. 5B to a flared, expanded shape. The anchoring skirt 26 comprises an inner stent frame 80, a fabric covering 82, and a band-like lower sealing flange 84. The stent frame 80 assembles within a tubular section of fabric 82, which is then drawn taut around the stent frame, inside and out, and sewn thereto to form the intermediate cloth-covered frame 88 in FIG. 5. During this assembly process, the stent frame 80 is desirably tubular, though later the frame will be crimped to a conical shape as see in FIG. 7B for example. A particular sequence for attaching the tubular section of fabric 82 around the stent frame 80 includes providing longitudinal suture markers (not shown) at 120° locations around the fabric to enable registration with similarly circumferentially-spaced, commissure features on the stent frame. After surrounding the stent frame 80 with the fabric 82, a series of longitudinal sutures at each of the three 120° locations secure the two components together. Furthermore, a series of stitches are provided along the undulating upper end 86 of the stent frame 80 to complete the fabric enclosure. In one embodiment, the tubular section of fabric 82 comprises polytetrafluoroethylene (PTFE) cloth, although other biocompatible fabrics may be used. Subsequently, the lower sealing flange 84 shown in FIG. 6 is attached circumferentially around a lower edge of the intermediate cloth-covered frame 88.

FIG. 7A shows the valve member above the cloth-covered anchoring skirt and schematically shows one method of couple the two elements using sutures. FIG. 7B illustrates the inner plastically-expandable stent frame 80 with cloth covering removed to indicate a preferred pattern of coupling sutures passed therethrough. The anchoring skirt 26 preferably attaches to the sewing ring 62 during the manufacturing process in a way that preserves the integrity of the ring and prevents reduction of the valve's effective orifice area (EOA). Desirably, the anchoring skirt 26 will be continuously sutured to the ring 62 in a manner that maintains the contours of the ring. In this regard, sutures may be passed through apertures or eyelets 92 arrayed along the upper or first end 86 of the inner stent frame 80. Other connection solutions include prongs or hooks extending inward from the stent, ties, hook-and-loop fasteners (e.g., Velcro® fasteners), snaps, adhesives, etc. Alternatively, the anchoring skirt 26 may be more rigidly connected to rigid components within the prosthetic valve member 24.

The construction steps described above in FIGS. 1-7 are relatively detailed and time-consuming. Current hybrid valves such as described above take 11-12 hours total to build. This includes building a valve member, as in FIGS. 1-3, which takes approximately 7.5 hours, and then covering the stent frame 80 with cloth and attaching it to the valve member, which combined take another 3-4 hours of time. It would therefore be desirable to reduce the labor hours to build such a valve.

Moreover, the aforementioned hybrid valve system does not have expandability during a valve-in-valve (ViV) procedure due to both the relatively rigid band subassembly 40 as well as the anchoring stent frame 80. Some attempts at making prosthetic valves expandable for ViV are known, but the resulting valve is expensive and difficult to build. Consequently, the present application discloses a number of configurations of hybrid valves and methods of making that simplify the assembly and result in a ViV-adapted hybrid valve.

Figure 8A:
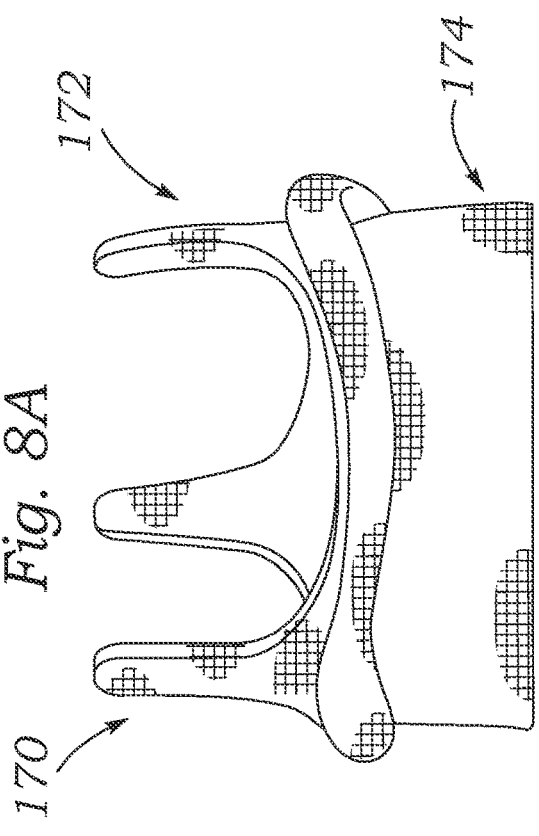
Figure 8B:
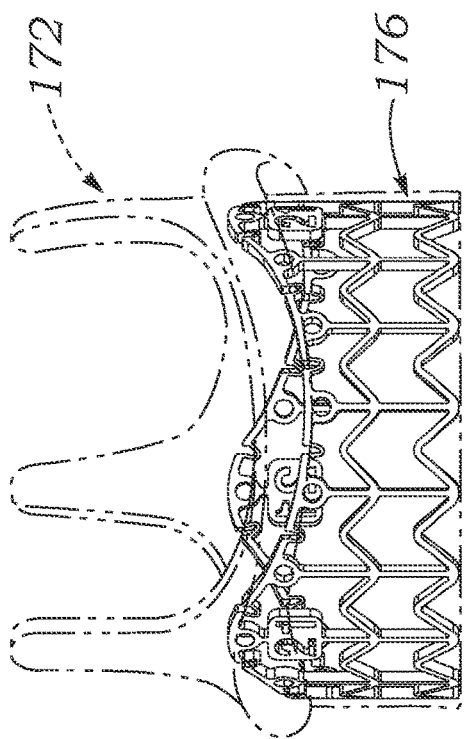
FIG. 8B shows an anchoring skirt therefor with a valve member in phantom.
Figure 8C:
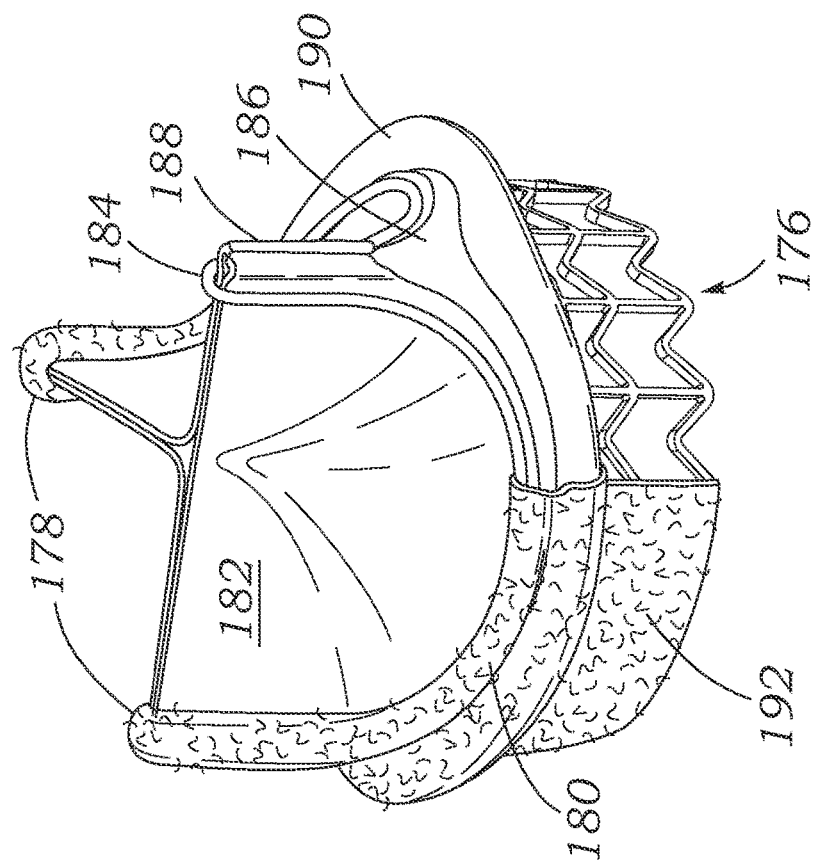
FIG. 8C is a perspective view of the prosthetic heart valve with portions cutaway to reveal internal structural leaflet supports.

FIGS. 8A-8C illustrate a hybrid prosthetic heart valve 170 of the present application, which includes an upper valve member 172 coupled to a cloth-covered anchoring skirt 174. FIG. 8B shows the valve member 172 in phantom to illustrate the contours of an expandable frame 176 of the anchoring skirt 174, and FIG. 8C is a perspective view of the entire heart valve 170 with portions at one commissure post 178 cutaway to reveal internal structural leaflet supports.

The valve member 172 of the hybrid prosthetic heart valve 170 shares some structural aspects with the prior art valve member illustrated in FIG. 3. In particular, there are three upstanding commissure posts 178 alternating with three arcuate cusps 180 curving in an inflow direction. Three flexible leaflets 182 are supported by the commissure posts 178 and cusps 180 and extend across a generally cylindrical flow orifice defined therewithin. The leaflets 182 are attached to an up and down undulating typically metallic wireform 184 via a cloth covering. As with earlier valve constructions, the upstanding posts 186 rise up adjacent to and just outside of the commissures of the wireform 184, and outer tabs 188 of the leaflets 182 extend underneath the wireform, wrap around the posts, and are secured thereto with sutures.

In the illustrated embodiment, the heart valve 170 also includes a highly compliant sealing ring 190 extending outward therefrom at approximately the interface between the valve member 172 and the anchoring skirt 174. The sealing ring 190 as well as the expandable frame 176 are covered with a fabric 192 that helps prevent leakage around the outside of the valve once implanted. Furthermore, the sealing ring 190 is also suture-permeable and may be used to secure the valve in place in the native annulus.

Figure 9A:
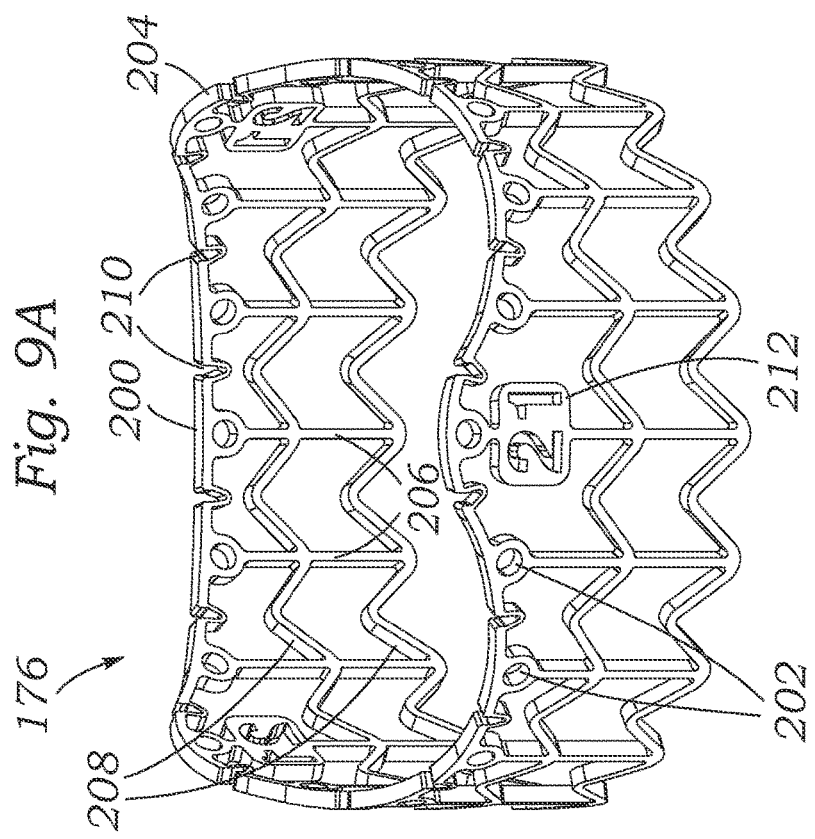
FIGS. 9A-9C are perspective views of an exemplary anchoring skirt for use in the hybrid prosthetic heart valve of FIGS. 8A-8C.
Figure 9B:
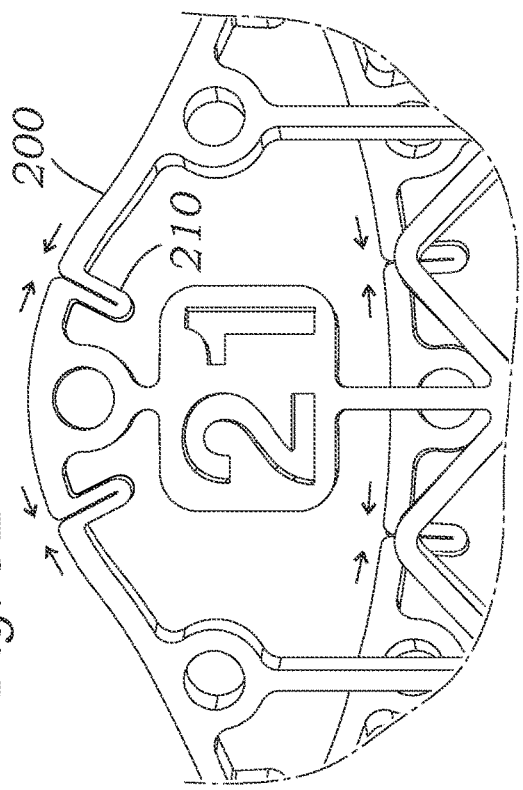
Figure 9C:
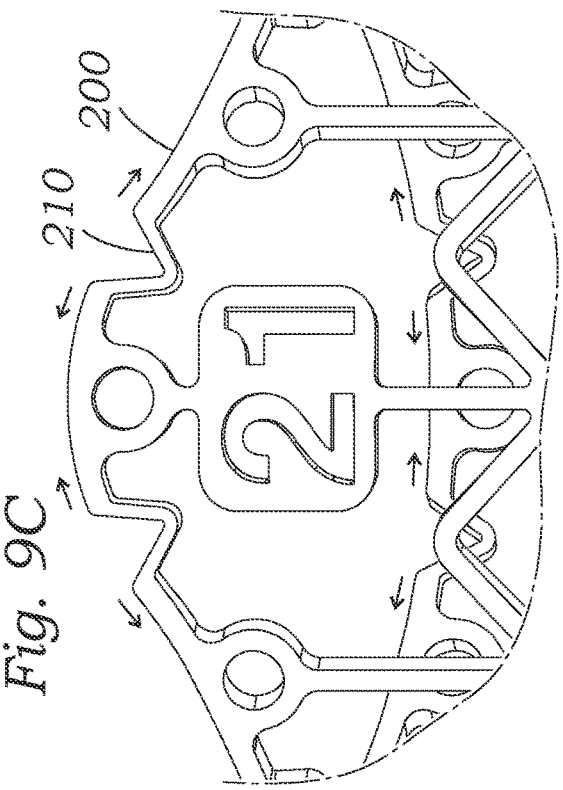

FIGS. 9A-9C illustrate details of the exemplary expandable frame 176 for use in the hybrid prosthetic heart valve 170 of FIGS. 8A-8C.

With specific reference to FIG. 9A, the lower frame 176 is shown in perspective and includes a plurality of circumferential row struts connected by a series of spaced axial column struts. Specifically, an upper or outflow row strut 200 extends continuously around a periphery of the frame 176, and preferably follows a gently undulating path so as to match a similar shape of the underside of the upper valve member 172 (FIG. 8B). As seen in FIG. 9A, three peaks 204 along the upper row strut 200 correspond to the locations of the commissures 178 of the valve 170. In general, the lower frame 176 attaches to an inflow end of the upper valve member 172, and preferably directly to or to fabric covering the internal support frame. The lower frame 176 is initially generally tubular and expands to be somewhat conical with the free end farthest from the upper valve member 172 expanding outward but the end closest remaining the same diameter.

The upper row strut 200 includes a plurality of eyeholes 202 evenly spaced apart and located just below the top edge thereof that are useful for securing the frame 176 to the fabric of the underside of the valve member 172. A series of axial column struts 206 depend downward from the upper row strut 200, and specifically from each of the eyeholes 202, and connect the upper row strut to two lower row struts 208. The lower row struts 208 circumscribe the frame 176 in zig-zag patterns, with an inverted "V" shape between each two adjacent column struts 206. The lower row struts 208 preferably traverse horizontally around the frame, and the length of the column struts 206 thus varies with the undulating upper row strut 200.

As mentioned above, the lower frame 176, in particular the inflow end thereof, may be plastically expanded, such as by balloon expansion, and may be formed of a plastically expandable material, for example, stainless steel or cobalt-chromium (e.g., Elgiloy® alloy). Alternatively, the lower frame 176 may be self-expanding, such as being formed from nitinol. In a conventional Edwards Intuity® valve, the upper row strut 200 is generally ring-like without capacity for compression or expansion. In the illustrated frame 176, on the other hand, a series of spaced notches 210 are provided that permit expansion and contraction. That is, circumferential segments of the strut 250 are interrupted by the V-shaped notches 210 that permits a limited amount of expansion, perhaps 3 mm in diameter, to accommodate a supplemental expandable valve to be inserted and expanded therein. More particularly, the upper row strut 200 (outflow end) of the frame 176 defines a nominal diameter seen in FIG. 9A that enables functioning of the valve member 172. The upper row strut 200 is radially compressible from the nominal diameter to a smaller contracted diameter to enable compression of the outflow end of the frame 176 during delivery of the heart valve. The upper row strut 200 is also radially expandable from the nominal diameter to a larger expanded diameter upon application of an outward dilatory force from within the stent frame such as in a valve-in-valve procedure.

It should be understood that the preferred embodiment of the hybrid prosthetic heart valve 170 is configured for surgical delivery, which differs from transcatheter or transapical delivery. In the latter cases, prosthetic heart valves are formed of structures and materials that enable substantial compression of the valve into a relatively small diameter profile, to enable delivery through the vasculature (e.g., transcatheter) or directly into the heart through an introducer (e.g., transapical). The hybrid prosthetic heart valve 170, on the other hand, is typically delivered via open heart surgery or a less invasive version thereof, such as through a mid-thoracotomy. "Surgical" delivery of heart valves requires that the heart be stopped and the patient be placed on cardiopulmonary bypass, while transcatheter and transapical procedures may be done on a beating heart. Therefore, the hybrid prosthetic heart valves 170 disclosed herein are only compressible to a limited degree, to enable a smaller delivery profile, but not totally compressible.

As shown in FIG. 9B, the modified frame 176 can be collapsed to a pre-determined minimum diameter for delivery and expanded to a pre-determined maximum diameter during a valve-in-valve procedure. More specifically, the upper row strut 200 of the illustrated frame 176 may be collapsed by 2 mm relative to the nominal diameter for ease of delivery by compressing the V-shaped notches 210 as indicated. Because the notches 210 can only be compressed until the two corners meet, the frame 176 can only be collapsed by a predetermined amount. The exemplary frame 176 is specifically designed to be collapsible to ease insertion through small incisions when the valve is implanted and for ease of seating in the annulus. The amount of collapse could be as large as about 40-50% by diameter, but would more preferably be about 2-3 mm, or between about 7-20% for heart valves having nominal operating diameters between about 19-29 mm. A compression of 2 mm in diameter, for example, corresponds to a change in circumference of about 6.28 mm. The stent frame is divided into 18 segments around its circumference by the axial column struts 206. Therefore, by placing an initial gap of 0.35 mm (6.28 mm/18) in each segment, the frame can collapse by 2 mm in diameter before adjacent segments make contact and hence prevent further compression.

FIG. 9C discloses that the upper row strut 200 of the illustrated frame 176 may be subsequently expanded by up to 3 mm relative to a nominal diameter during a valve-in-valve procedure. Because of the configuration of the upper row of struts, the outflow portion of the frame cannot be expanded more than 3 mm. That is, the V-shaped notches 210 eventually straighten out, which prevents further expansion. Desirably, the frame is designed to expand 3 mm in diameter beyond its nominal diameter. The nominal diameter is defined when the notches 210 are V-shaped, prior to either contraction or expansion. Similar to the gaps for limiting compression, the 3 mm in expansion corresponds to an about 9.42 mm (3 mm×π) change in circumference. Therefore, each of the 18 segments limits expansion to 9.42 mm/18=about 0.52 mm. In this example, the length of the "V" shaped struts connecting each segment are thus 0.52 mm+0.35 mm (from the compression gaps)=0.87 mm. During a valve-in-valve expansion, the expansion of the stent frame would be limited by the expansion-limiting struts at the point where they became straight across the gap between adjacent frame segments.

If it is not desired to have the frame collapsible but expansion is still desired, the gaps could be reduced to the practical limit of laser cutting, for example, about 25 µm. With 18 gaps of 25 µm, the total amount of compression would be (18×25 µm/π)=0.143 mm (about 0.006").

In contrast, some earlier designs simply removed the upper row of struts that defines the outflow diameter of the frame. Such a frame configuration had no built-in way to limit the maximum expansion of the valve during a valve-in-valve procedure. Additionally, there could be an advantage to having hybrid valves that are collapsed by a limited amount, for example, about 2-3 mm, for easier insertion. While a frame without an upper row of struts could be collapsed, there is no built-in limit the amount of compression. It might be desirable to have the maximum compression amount limited as disclosed herein for consistency and for preventing physicians from trying to collapse the valve more than it can safely be collapsed.

In addition, a number of valve-type indicators 212 are integrated into the frame 176 at locations around its circumference, such as three valve size indicators. In the illustrated embodiment, the valve size indicators 212 comprise small plate-like tags inscribed with the numerical valve size in mm, for example 21 mm in the illustrated embodiment. The use of any alphanumeric characters and/or symbols that signify size or other feature of the valve are contemplated. The frame 176 may be laser cut from a tubular blank, with the plate-like size indicators 212 left connected to one more of the struts. As shown, the size indicators 212 are located just below the peaks 204 of the undulating upper row strut 200, connected between the corresponding eyehole 252 and the descending column strut 206. There are thus three size indicators 212 spaced about 120° apart around the frame 176. This location provides additional space between the upper row strut 200 and the adjacent lower row strut 208. The inscribed or cutout valve size numerals are sufficiently large to be visualized with X-ray, Transesophageal Echocardiogram (TEE), or other imaging modality. In one embodiment, the valve size numerals are from about 1.5 mm to about 2 mm in height, for example, about 1.75 mm in height.

FIG. 10A is an exploded perspective view of components of an alternative hybrid prosthetic heart valve 300. The alternative heart valve 300 does away with an internal stent or support frame previously shown as the composite bands 42, 48 in FIG. 1A, for example. The composite band structure was the primary source of circumferential rigidity to the heart valves in which they were employed, and thus an expansion structure enabled valve-in-valve procedures. The alternative hybrid heart valve 300 includes a lower compressible/expandable frame 302, as before, separate commissure posts 304 that are secured to the frame, and an undulating wireform 306 supporting flexible leaflets 308, also as before.

FIG. 10B shows a subassembly 310 including the wireform 306 juxtaposed with the three leaflets 308, and an "integrated" subassembly 312 of the expandable frame 302 with the commissure posts 304 attached thereto. Each of the flexible leaflets 308 has two tabs 309, and pairs of tabs on adjacent leaflets are shown projecting through (under) the inverted V-shaped commissures of the wireform 306. These pairs of tabs 309 then wrap around one of the upstanding commissure posts 304 of the subassembly 312, which are located adjacent to and radially outward from the wireform commissures. The subassemblies 310, 312 are eventually covered with biocompatible fabric such as polyester, and the pairs of tabs 309 and commissure posts 304 are secured to each other with a cloth covering (see FIG. 13).

Due to the attachment of the commissure posts 304 to the frame 302 the subassembly 312 integrates the frame and commissure posts, while as described below, an "integrated" frame may mean that the commissure posts are integrally formed of the same homogeneous material as the rest of the stent frame. Integrated in this sense meaning the two components are securely attached together prior to assembly with the wireform/leaflet subassembly 310, either by securing the two parts or forming them at the same time from the same material. Furthermore, a hybrid heart valve with an "integrated" frame means that the frame provides both the expandable skirt frame as well as commissure posts to which the leaflets attach, without any additional structural bands, such as the metal band 48 seen in FIG. 1A. With this configuration, the number of parts in the valve is reduced, which reduces assembly time and expense.

Figure 10C:
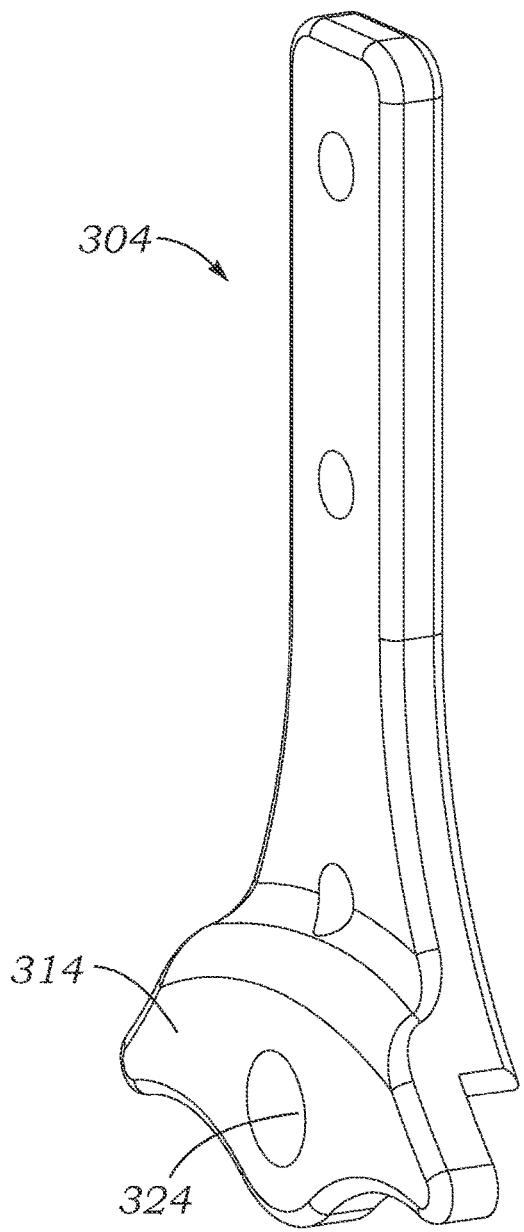
FIGS. 10C and 10D show details of separate commissure posts.
Figure 10D:
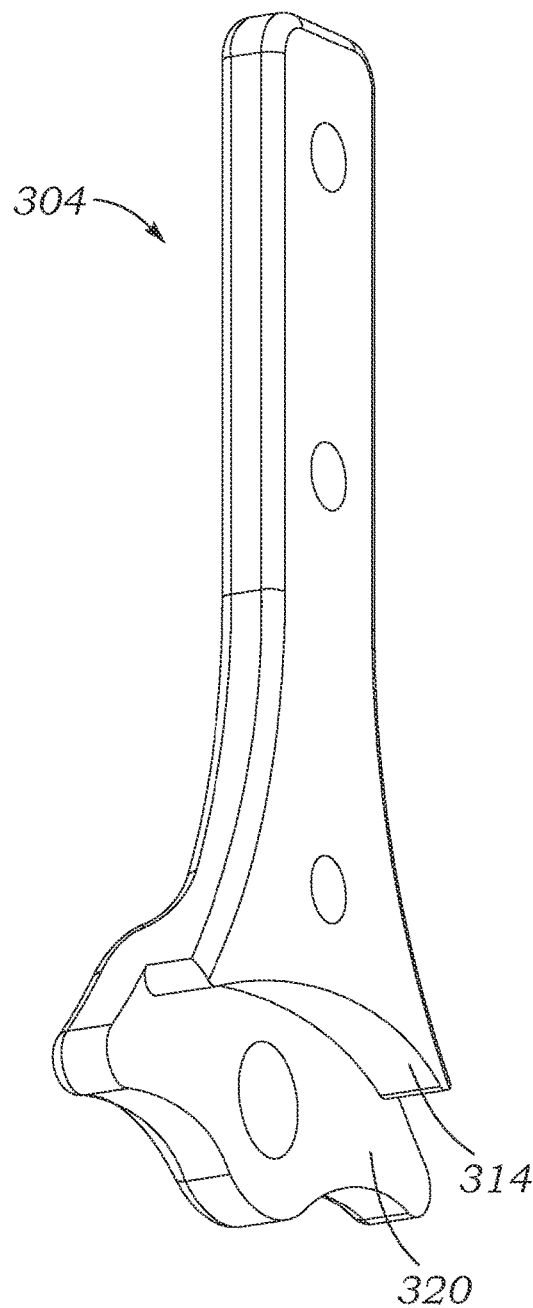

FIGS. 10C and 10D illustrate a commissure post 304 from an outer and an inner perspective, respectively. A lower end of each of the commissure posts 304 includes a concave ledge 314 that matches the contour of one of the peaks 316 in the undulating upper row of struts 318 of the expandable frame. As seen in FIG. 10B, an outer plate 320 below each of the concave ledges 314 of the commissure posts 304 extends downward on the outside of the expandable frame 302. Sutures 322 secure the commissure posts 304 to the frame 302 via suture holes 324 that align with eyeholes 326 at the peaks 316 of the undulating upper row strut 318. This shape matching followed by covering with fabric provides a relatively stable arrangement of the commissure posts 304 in the integrated frame subassembly 312.

FIG. 11 is another exploded perspective view of subassemblies of the alternative hybrid prosthetic heart valve 300. In this view, the wireform in the subassembly 310 of the wireform and leaflets has been covered with fabric, and features an outwardly projecting flap 330. The fabric flap 330 is used to secure the wireform/leaflet subassembly 310 to the subassembly 312 of the expandable frame 302 and commissure posts 304. Furthermore, a suture-permeable sealing ring 332 may be attached such as by sewing at the juxtaposition between the two subassemblies 310, 312.

The relative positions of the wireform 306 and the frame/commissure post subassembly 312 is seen in FIG. 12, and also in further detail in FIGS. 12A-12D, with the commissure posts 304 immediately outside of the commissures of the wireform 306. Finally, FIG. 13 is a perspective view of the finished hybrid prosthetic heart valve 300 entirely covered with fabric.

The removal of the aforementioned stent bands and attachment (integration) of the commissure posts 304 directly to the frame 302 greatly simplifies construction, reduces labor hours, lowers the radial profile of the valve by ~1.6 mm, and allows for expansion during a valve-in-valve procedure. A preferred construction sequence involves attaching the sealing ring 332 to the expandable frame 302, along with three cloth-covered commissure posts 304, then attaching this assembly to the wireform/leaflet subassembly 310 during final assembly.

The commissure posts 304 disclosed have specific features that interface with the frame 304 to add stability to the posts in all directions. That is, the specific surfaces 314, 320 that mate with the corresponding peaks 316 on the frame 302 as well as the holes 324 that allow the posts to attach with sutures 322 to the frame provide excellent stability in all directions for subsequent covering with fabric. The commissure posts 304 could be molded from polyester or some other biocompatible material into the shape shown here, or even produced using 3D printing.

A hybrid valve 340 built using the disclosed methods is shown in FIGS. 14A and 14B with all but flexible leaflets 342 covered with cloth. The improved valve construction disclosed herein eliminates a separate stent subassembly by combining the functions of that assembly (supporting the leaflets from underneath as well as from the sides in the commissure area, and attachment of the sewing ring insert) with the stent frame assembly. As will be explained, the main components of the hybrid valve 340 include a wireform 344 having alternating cusps and commissures that supports the leaflets 342, a lower expandable frame 346 integrated with commissure posts 348, and preferably a sealing ring 350 around the periphery of the cusps of the wireform 344. Several steps in the assembly process will now be described.

FIG. 15A shows the first step in the disclosed method of hybrid valve construction. A piece of PTFE tubular cloth 352 is first partially inverted and placed over the generally tubular stent frame 346 from the bottom, thus covering the inside, outside, and bottom of the frame. Subsequently, the cloth 352 is sewn to the frame 346 through frame holes and around a top circumferential row of struts 354 using an in-and-out stitch with double PTFE thread. FIG. 15B shows the cloth 352 pulled back on the inside and outside after sewing is complete, thereby exposing the top of the stent frame 346. More particularly, the top circumferential row of struts 354 is left partly exposed; at least three peaks intermediate three valleys of the undulating row.

FIG. 16A shows the stent frame 346 covered in the cloth 352 and with a sewing ring insert 356 placed adjacent the top row of struts 354. The cloth layers below the sewing ring 356 have been rough cut, which is acceptable as they are subsequently covered in an outer layer of cloth, thus eliminating the need to "finish" the PTFE cloth in that area. An alternative method would be to fold those layers and finish them on either the top or bottom of the sewing ring.

In FIG. 16B, the sewing ring insert 356 has been stitched to the top of the stent frame 346 in 6 locations to give it a desired scalloped shape. Six locations would be a minimum to define the high (commissures) and low (cusp centers) points of its desired shape. It could be attached at more locations to better define its shape. The PTFE cloth 352 from the inside of the stent frame 346 has been inverted over the sewing ring insert 356 and formed by hand to follow the scalloped shape of the insert. Subsequent to conforming the cloth to the insert as shown, both the inner and outer layers of cloth are sewn together (between the stent frame and the insert).

Figure 17:
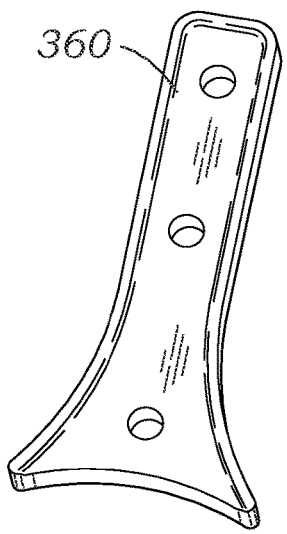
FIG. 17 is a perspective view of a separate commissure post.
Figure 18:
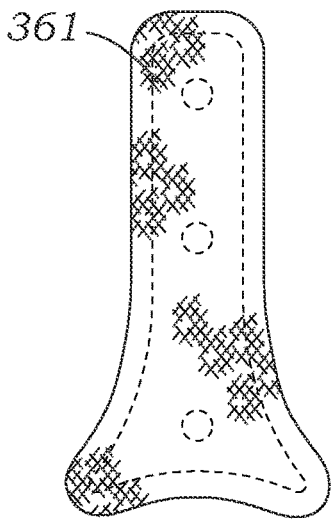
FIG. 18 is the commissure post covered with cloth.

After the sewing ring formation as shown in FIG. 16B, the next step is to cover three polymer (e.g. PET) commissure tip inserts 360, shown in FIG. 17, with cloth 361, as shown in FIG. 18. Because these inserts 360 are simple 2D parts, they could potentially be sewn on a machine, or "socks" could be knitted to fit over them. Another option could be to use a different cloth, such as PET-based cloth, which could be laser cut and fused to make the covers for the inserts.

Figure 19A:
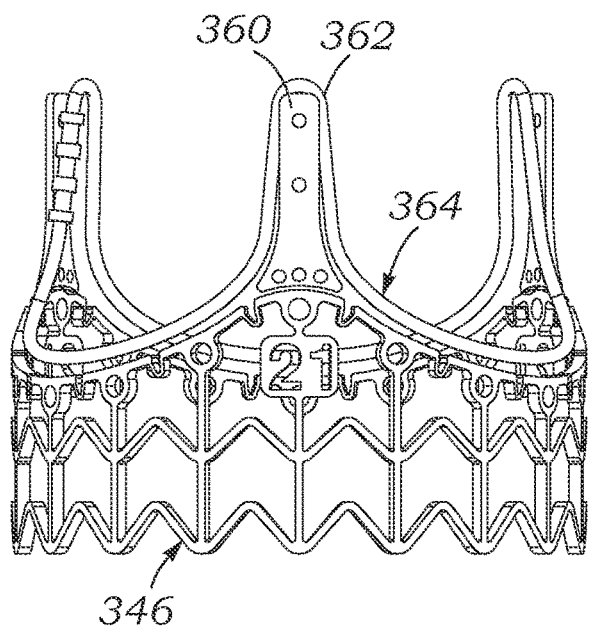
FIGS. 19A and 19B are elevational views of an exemplary integrated frame member of the present application.
Figure 19B:
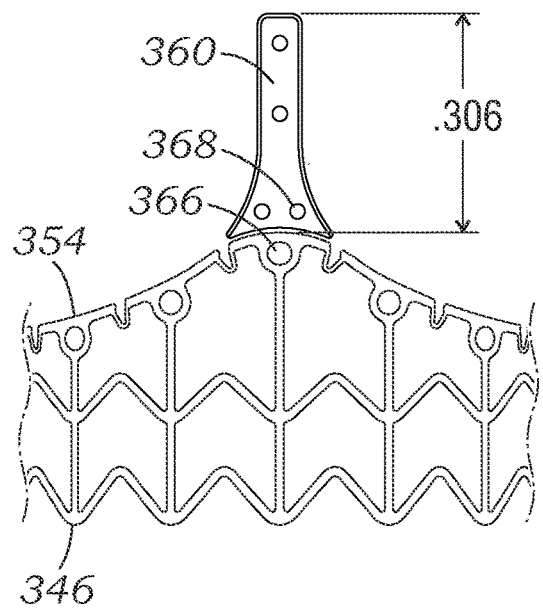

FIGS. 19A and 19B shows how the inserts 360 sit with respect to the stent frame 346 and outside of the commissures 362 of a wireform 364. The cloth is not shown in the sketch. The inserts 360 sit directly over the peaks of the upper row of struts 354 of the stent frame 346. The tip inserts 360 and stent frame 346 could be sewn together through holes 366 in the stent frame and a lower hole 368 in the inserts, through their respective layers of cloth. This provides a high degree of vertical stability to the commissures of the assembly. FIGS. 19A and 19B show two different patterns for the holes 368 in the inserts 360, two or three toward the lower end, while FIGS. 17 and 18 show a single hole. Of course, other arrangements are contemplated.

After the cloth-covered commissure inserts 360 are attached to the stent frame/sewing ring assembly, final assembly would be performed. Final assembly would include stitches from below the sewing ring insert 356 (see FIG. 16A) through its hinge point, through the leaflets and wireform cloth, then down through all layers as an in-and-out stitch.

Figure 20:
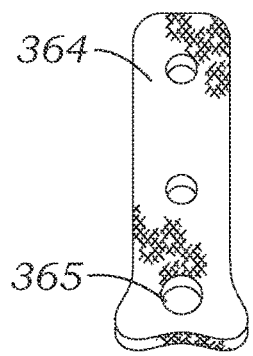
FIG. 20 is an alternative commissure post.

One method of creating commissure inserts uses a polyester (or other material) tip piece 363, similar to that used in the Carpentier-Edwards Model 2700 heart valve, as shown in FIG. 20. The tip piece 363 would have at least one hole 365 in the bottom to facilitate attachment to the expandable stent frame after cloth covering, as well as other holes for securing the cloth, and securing the insert to the wireform cloth.

Figure 21:
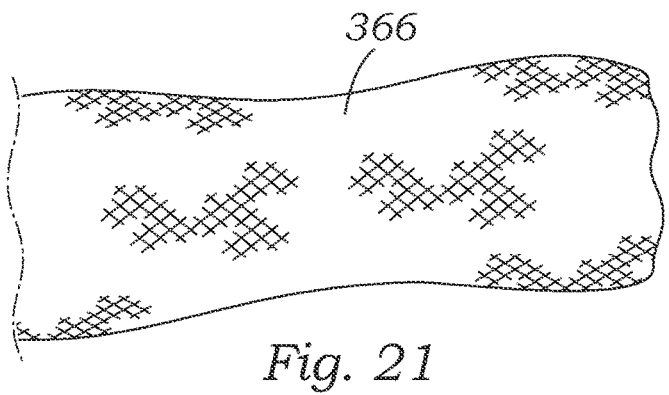
FIG. 21 is a tubular legs of fabric used to cover the separate commissure posts.

FIG. 21 shows an example of a PET tubular cloth 366, which could be used to cover the component shown in FIG. 20. The ends of the tube can be knitted closed, as is done on prior art annuloplasty rings, or fused closed with ultrasonic, laser, or heat methods. With one end closed, the piece 364 from FIG. 20 can be inserted from an open end. The cloth 366 can then be folded over to form multiple layers on one side tip piece for subsequent leaflet attachment.

Figure 22A:
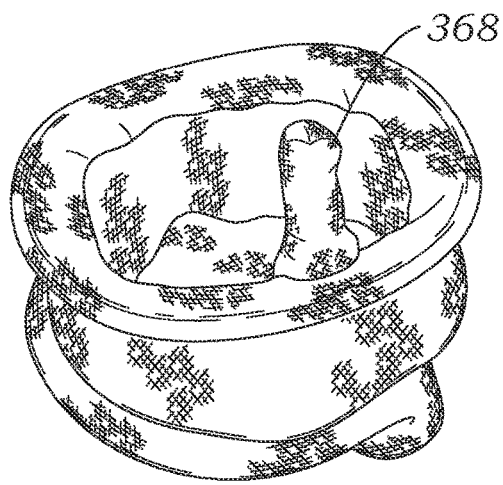
FIGS. 22A and 22B are perspective views of a cloth-covered commissure post secured to an outflow edge of a cloth-covered anchoring frame member.
Figure 22B:
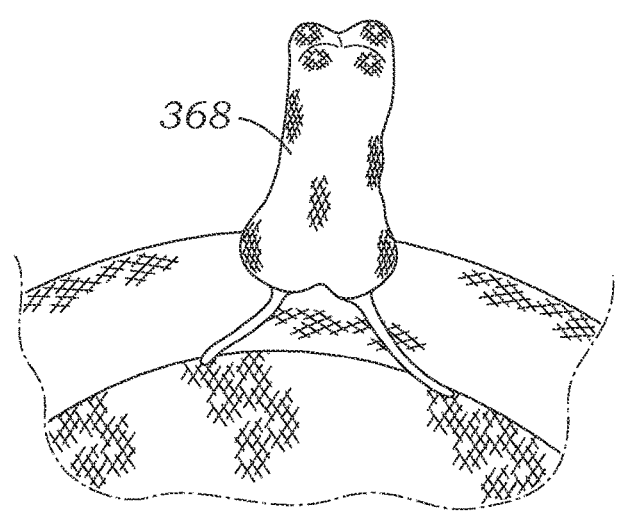

FIGS. 22A and 22B show a commissure insert 368 made in the fashion attached to a cloth-covered expandable stent frame described above. Three such commissure inserts would be attached to the cloth-covered stent frame, which would then be ready for final assembly with the wireform-leaflet assembly. A second method of making commissure inserts uses a non-woven fabric such as Reemay® spun-bonded polyester.

Figure 23:
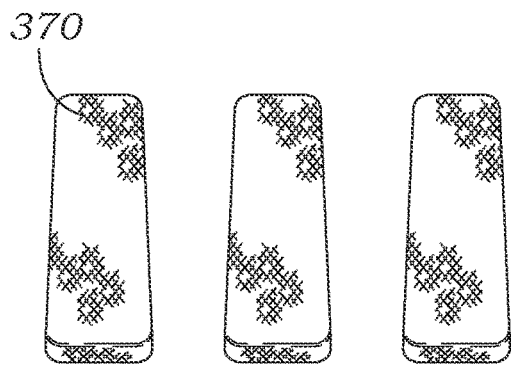
FIG. 23 illustrates alternative commissure posts.
Figure 24:
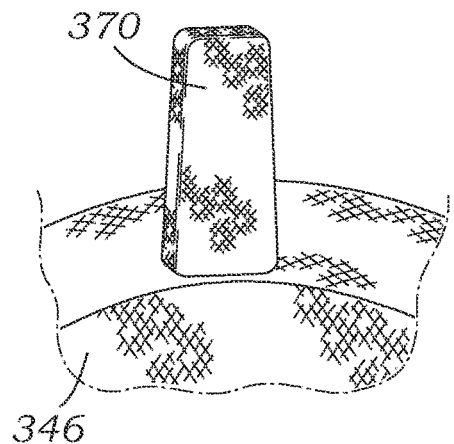
FIG. 24 shows one alternative commissure post secured to an outflow edge of a cloth-covered anchoring frame member.

FIG. 23 shows solid fabric inserts 370 made in this manner. The inserts 370 can simply be die (or laser, etc.) cut from non-woven fabric sheet of the desired thickness and porosity. These inserts 370 would be immediately ready to attach to the cloth-covered stent frame 372 as shown in FIG. 24. As an alternative to making them from a homogenous sheet, they could be made from a composite that had, for example, a very dense and stiff layer that could face the inside of the valve to add support and minimize leakage, and a less dense layer on the outside that would be easy to stitch to during final valve assembly. For even more stiffness, the composite could contain a layer of polyester sheet, either inserted into a pocket cut into a single, thick section of fabric, or as a layer in a composite structure.

FIGS. 25-31 illustrate alternative integrated anchoring skirt and commissure post subassemblies. As described above with respect to FIGS. 10-13, the subassembly 312 shown in FIG. 10B eliminates the need for annular structural bands, which bands provide stability and rigidity but which impede the ability of the valve to expand post-implant. Each of the alternative subassemblies shown in FIGS. 25-31 also eliminate the need for the structural bands, and further integrate the anchoring skirt and the commissure posts.

FIG. 25A shows a still further assembly 400 of the structural components of a hybrid prosthetic heart valve having an integrated frame member 402 much like those described above but formed of a single piece. A schematic wireform 404 is shown situated on top of the frame member 402 in FIG. 25A, with flexible leaflets and a cloth cover not shown and representing a wireform/leaflet subassembly such as shown at 310 in FIG. 11. The schematic wireform 404 is shown with an outwardly extending sewing flange 406, which may be formed by joined lengths of two fabric tabs that wrap around and cover the wireform. When covered with cloth, the frame member 402 serves as the supportive component for the wireform, leaflets and sealing ring. Further, when covered with cloth, the frame member 402 provides an effective seal against paravalvular leaking (PVL) and circumferential stability to the valve.

The integrated frame member 402, which is also shown in FIGS. 25B-25D, comprises a lower expandable skirt portion 410, an upper annulus band 412, and leaflet support posts 414. The skirt portion 410 comprises a number of chevron patterned or V-shaped struts that can be easily crimped and then expanded. The annulus band 412 provides real estate for the attachment of a sealing ring (not shown), and preferably includes a series of holes around its circumference through which to pass sutures connecting the sealing ring. The integrated frame member 402 includes multiple cuts that enable post-implant expansion and may be laser-cut from a suitable metal such as Elgiloy and electro-polished.

The frame member 402 is desirably formed from a tubular blank of a suitable material, and has a generally circular inflow or lower edge and an undulating outflow or upper edge. More particularly, the upper edge defines three arcuate cusp portions 416 intermediate three upstanding commissure posts 418. The undulating upper edge is shaped to closely fit underneath the wireform 406. After assembling the frame member 402 with the rest of the heart valve components, the skirt portion 410 is typically crimped in a generally conical manner such that its lower edge has a smaller diameter than its upper edge.

Compression/expansion sections 420 along the annulus band 412 are also added to enable a limited collapse of the frame member 402 during delivery. The compression/expansion sections 420 comprise slits formed in the upper edge of the frame member 402 that have spaces enabling a limited compression, and also permit expansion. In a preferred embodiment, solid segments 422 spaced around the annulus band 412 are connected by thin inverted U-shaped bridges 424.

As seen in FIG. 25D, the frame member 402 further includes a number of slits in the region of the commissures 418 to facilitate expansion in general flexibility of the frame member. An elongated central slit 426 extends nearly the entire height of each of the commissures 418. Regions of expandable circumferential struts 428 are positioned within the skirt portion 410 axially aligned with both the compression/expansion sections 420 and the central slits 426. When an outward radial force is applied from within the heart valve having the frame member 402, the annulus band 412 permits expansion because of both the sections 420 and slits 426. Additionally, short arcuate slits 430 are formed at the base of each of the commissure posts 418, generally following a truncated undulating line joining the cusp portions 416. These slits 430 reduce the radial stiffness of the posts 418 such that most of the physiological load absorbed by the flexible leaflets is transferred to the wireform 406, rather than to the posts.

Despite the arcuate slits 430 in the frame member 402 of FIGS. 25A-25D, there are concerns that such an integrated frame design will stiffen the wireform commissure post area, thus altering the load carry mechanism of proven valve platforms. To alleviate such concerns, the three commissure posts may be made of three separate pieces, preferably using polymeric material, such that when connected with the underlining metal frame with sutures, there will not be metal to metal contact.

For instance, FIGS. 26A-26D illustrate an alternative frame member 440 that is configured about the same as the frame member 402, but has separate commissure posts 442.

Figure 26A:
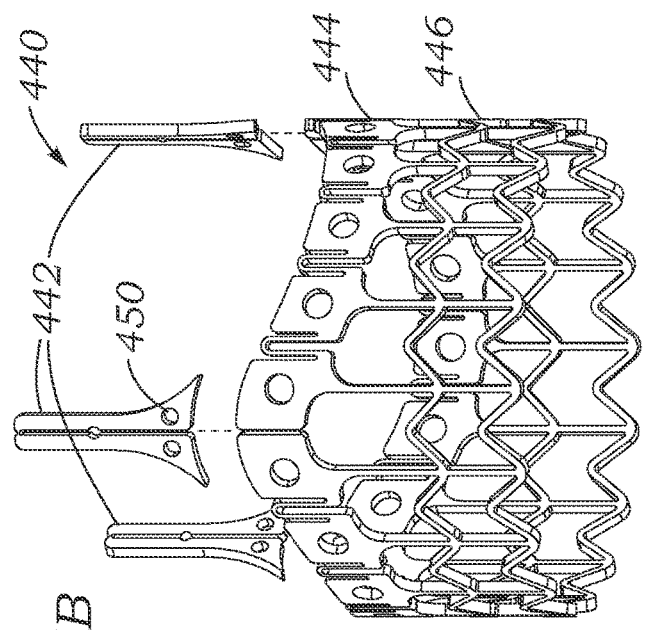
FIGS. 26A-26D are several views of an alternative integrated frame member much like that shown in FIGS. 25A-25D but with commissure posts that are separated from a lower expandable frame.
Figure 26B:
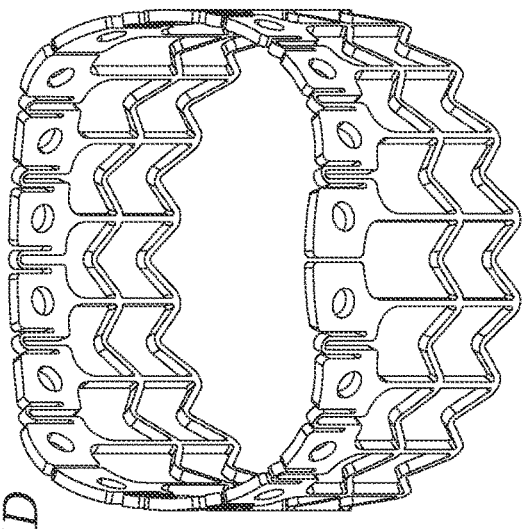
Figure 26C:
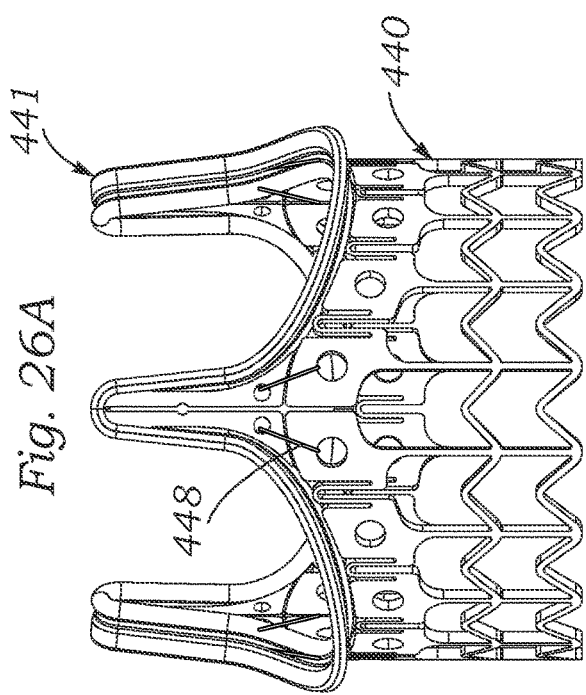
Figure 26D:
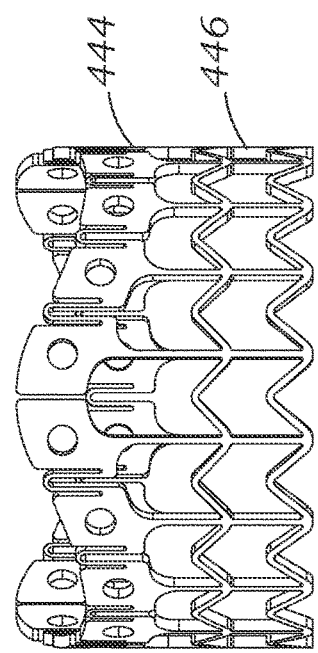

The frame member 440 is shown situated just below a wireform assembly 441 in FIG. 26A. As seen in FIGS. 26C-26D, the annulus band region 444 and the in-flow strut region 446 are exactly same as that of the frame member 402. The only difference is separate commissure posts 442 preferably made of plastic material that will be sewn together with the frame member 440 using sutures 448 before being covered with cloth. A pair of attachment holes 450 is desirably formed in each of the commissure posts 442 for this purpose. As before, the crimpable and expandable frame member 440 without commissure posts is laser-cut and electropolished.

Although the ability to compress and expand the frame members may be an advantage, the present application also contemplates integrated frame members for a hybrid prosthetic heart valves that are not either expandable or compressible. FIGS. 27A-27B show an assembly 460 of the structural components of a hybrid prosthetic heart valve including an integrated frame member 462 with a lower expandable skirt portion 464, an upper annulus band 466, and leaflet support posts 468. The annulus band 466 provides real estate for the attachment of a sealing ring (not shown). As before, the integrated frame member 462 may be laser-cut from a suitable metal tube such as Elgiloy and electro-polished. A wireform 470, such as in the subassembly 310 in FIG. 11, is illustrated just above the undulating upper end of the frame member 462, with flexible leaflets and a cloth cover not shown for clarity.

As seen best in FIG. 27B, the frame member 462 has an outflow or upper edge 472 without capacity for either compression or expansion. That is, a plurality of solid segments 474 spaced around the annulus band 462 are connected by small solid bridges 476. Each of the solid segments 474 preferably has a through hole 478 for use in an attaching a sewing ring around the periphery thereof.

FIG. 28A shows another assembly 480 of the structural components of a prosthetic heart valve including a non-compressible, non-expandable integrated frame member 482 much like the one in FIGS. 27A-27B, but with separated commissure posts 484. Several suture holes 486 in the commissure posts are also added to help secure the commissure posts 484 to an annulus band 488 of the frame member 482, much like is shown in FIG. 26A.

FIG. 25A is a fully integrated frame member 402, with concerns over stiffened commissure posts. The frame member 442 shown in FIG. 26A alleviated that concern with three separate commissure posts 442, but those require sewing together with the expandable frame, which increases the time and steps when assembling the valve. In order to preserve the same load bearing characteristics of the existing commercial valve platforms, while still having a relative easy valve assembly procedure, the embodiments shown in FIGS. 29 and 31 are also contemplated.

FIG. 29 shows an assembly 500 that includes an expandable frame 502 much like the frame 176 described above with respect to FIG. 9A. The frame 502 is secured via sutures to a stent band 504 with upstanding commissures 506 to form an integrated frame member. This stent band 504 is essentially the inner band 95 from FIG. 1A, with suture holes 505 around its circumference to enable secure attachment to the top row of struts of the frame 502. An upper row of struts 508 includes regularly spaced compressible/expandable segments 510 to enable pre-implant compression, and post-implant expansion during a valve-in-valve procedure.

The assembly 500 is again crimpable and expandable. The stent band 504 is formed of a polymer (e.g., polyester) material that is breakable when in expansion force is applied within the valve. This makes the whole valve expandable for valve-in-valve applicable. Because of the polymer commissures 506, the valve load carrying characteristics will be exactly the same as the existing commercial valve platform, thus hydrodynamic performance and durability of the valve shall be the same as the existing commercial valve as well. The relative position of the polyester band and the expandable frame can be assembled as illustrated in FIG. 29, with the stent band 504 positioned immediately above the frame member 502. Conversely, as seen in FIG. 31, the stent band 504 may be located partly radially within the frame 502, in an overlapping manner. This aligns the series of through holes 505 in the stent band 504 with eyeholes 512 provided in the frame 502, which greatly facilitates assembly, thus reducing time and expense.

Some Improvements Over Existing Designs:
1. Integrate the metal stiffener band, the stent frame and/or the polyester band together.
2. The commissure posts, the sewing ring section, as well as the chevron patterned strut section are expandable such that they expand uniformly without distorting the wireform.
3. Reduce the radial stiffness compared with the current heart valve frames so that a transcatheter valve balloon/frame can push the new valve open at least about 2 mm.
4. Integrated commissure posts for holding the leaflet tabs impose reduced or minimal forces on the leaflet, with most of the forces transferred to the wireform
5. No leakage path through the commissure post areas or the sewing ring attachment area.
6. Ease of locating and sewing/clipping/inserting the sewing ring on the frame.
7. During the crimping, expansion, and other manufacturing steps, the frame does not buckle/remains stable, especially at the commissure posts.
8. Crimpability at the annulus region reduces the profile of the valve during valve insertion.

Some Advantages:
1. Expandable hybrid prosthetic heart valves permit valve-in-valve procedures, improving valve performance.
2. Integrated design simplifies assembly, reducing labor and material costs.
3. Crimping the valve reduces its profile, which improves visibility during valve insertion and deployment, enhancing the user's experience.

While the disclosure references particular embodiments, it will understood that various changes and additional variations may be made and equivalents may be substituted for elements thereof without departing from the scope or the inventive concept thereof. In addition, many modifications may be made to adapt a particular situation or device to the teachings herein without departing from the essential scope thereof. Therefore, it is intended that the disclosure not be limited to the particular embodiments disclosed herein, but includes all embodiments falling within the scope of the appended claims.

What is claimed is:

1. A hybrid prosthetic heart valve having an inflow end and an outflow end, comprising:
   a valve member including an undulating wireform with alternating cusps and commissures supporting a plurality of flexible leaflets configured to ensure one-way blood flow therethrough; and
   an expandable inflow stent frame having a generally tubular portion with a radially-expandable inflow end and an outflow end that undulates with peaks and valleys corresponding to an inflow end of the wireform, wherein the stent frame outflow end defines an implant circumference that has a nominal diameter that enables physiological functioning of the valve member when implanted, and the stent frame outflow end includes integrated commissure posts homogeneously formed with the generally tubular portion and located adjacent to and radially outward from the wireform commissures, the stent frame being not homogeneously formed with the wireform and the generally tubular portion projecting in an inflow direction from an inflow end of the wireform, and further wherein the leaflets pass through the wireform commissures and attach to the commissure posts of the stent frame.

2. The prosthetic heart valve of claim 1, wherein the stent frame outflow end permits post-implant expansion from the nominal diameter to an expanded diameter larger than the nominal diameter upon application of an outward dilatory force provided by a dilation balloon or mechanical expander from within the outflow end larger than forces associated with normal physiological use.

3. The prosthetic heart valve of claim 2, wherein the stent frame outflow end is configured to be compressed to a constricted diameter smaller than the nominal diameter.

4. The prosthetic heart valve of claim 3, wherein the stent frame includes a plurality of circumferential row struts connected by a series of spaced axial column struts, and includes an outflow row strut that extends continuously around a periphery of the stent frame having peaks and valleys corresponding to the wireform, and the outflow row strut has a series of spaced V-shaped notches that permit limited expansion and contraction.

5. The prosthetic heart valve of claim 2, wherein the stent frame outflow end has a plurality of expandable sections spaced between each two commissure posts that facilitate the post-implant expansion.

6. The prosthetic heart valve of claim 2, wherein the stent frame includes a number of slits located at a base of each of the integrated commissure posts that facilitate the post-implant expansion.

7. The prosthetic heart valve of claim 2, further including an identifier on the stent frame visible from outside the body after implant that identifies the stent frame as having an expandable outflow end.

8. The prosthetic heart valve of claim 1, wherein the stent frame outflow end is non-compressible and non-expandable from the nominal diameter.

9. The prosthetic heart valve of claim 1, wherein the undulating wireform is fabric-covered, and the valve member has no additional structural bands.

10. The prosthetic heart valve of claim 1, wherein the stent frame is fabric-covered and further including a suture-permeable sealing ring enclosed by a portion of the fabric covering the stent frame and extending around a periphery of the outflow end of the stent frame.

11. A hybrid prosthetic heart valve having an inflow end and an outflow end, comprising:

a valve member including a plurality of flexible leaflets configured to ensure one-way blood flow therethrough; and an expandable inflow stent frame having a generally tubular portion with a radially-expandable inflow end and an outflow end secured to and projecting from an inflow end of the valve member, wherein the stent frame outflow end defines an implant circumference that has a nominal diameter that enables physiological functioning of the valve member when implanted, and wherein the outflow end of the stent frame includes integrated commissure posts, to which the leaflets attach, homogeneously formed with the generally tubular portion of the stent frame, the leaflets having tabs that extend outward and attach to the commissure posts of the stent frame, wherein the stent frame outflow end has an upper annulus band formed of solid sections interrupted by a number of axial slits and the stent frame has a skirt portion extending from the upper annulus band to the inflow end that comprises a number of chevron patterned or V-shaped struts.

12. The prosthetic heart valve of claim 11, wherein the valve member comprises a fabric-covered undulating wireform with alternating cusps and commissures supporting the leaflets, the valve member having no additional structural bands.

13. The prosthetic heart valve of claim 12, wherein the stent frame outflow end undulates with peaks and valleys corresponding to an inflow end of the wireform.

14. The prosthetic heart valve of claim 11, wherein the stent frame is fabric-covered and further including a suture-permeable sealing ring enclosed by a portion of the fabric covering the stent frame and extending around the upper annulus band of the stent frame.

15. The prosthetic heart valve of claim 11, wherein the stent frame outflow end permits post-implant expansion from the nominal diameter to an expanded diameter larger than the nominal diameter upon application of an outward dilatory force provided by a dilation balloon or mechanical expander from within the outflow end larger than forces associated with normal physiological use.

16. The prosthetic heart valve of claim 15, wherein the stent frame outflow end is configured to be compressed to a constricted diameter smaller than the nominal diameter.

17. The prosthetic heart valve of claim 16, wherein the upper annulus band comprises solid segments spaced around a periphery of the annulus band and connected by thin inverted U-shaped bridges partly defined by the axial slits.

18. The prosthetic heart valve of claim 15, wherein the upper annulus band has a plurality of expandable sections spaced between each two commissure posts that facilitate the post-implant expansion.

19. The prosthetic heart valve of claim 15, wherein one of the axial slits is located at a base of each of the integrated commissure posts that facilitate the post-implant expansion.

20. The prosthetic heart valve of claim 15, further including an identifier on the stent frame visible from outside the body after implant that identifies the stent frame as having an expandable outflow end.

* * * * *